(12) United States Patent
Hallila et al.

(10) Patent No.: US 9,989,040 B2
(45) Date of Patent: Jun. 5, 2018

(54) ACTUATOR AND METHOD FOR IMPROVING AN ACTUATOR

(71) Applicant: SYNOSTE OY, Espoo (FI)

(72) Inventors: Harri Hallila, Helsinki (FI); Juha Haaja, Espoo (FI); Antti Ritvanen, Helsinki (FI)

(73) Assignee: SYNOSTE OY, Espoo (FI)

( * ) Notice: Subject to any disclaimer, the term of this patent is extended or adjusted under 35 U.S.C. 154(b) by 365 days.

(21) Appl. No.: 14/824,304

(22) Filed: Aug. 12, 2015

(65) Prior Publication Data

US 2015/0369223 A1     Dec. 24, 2015

Related U.S. Application Data

(63) Continuation of application No. 14/767,106, filed as application No. PCT/FI2014/050119 on Feb. 18, 2014.

(51) Int. Cl.
| | |
|---|---|
| *F03G 7/06* | (2006.01) |
| *A61B 17/66* | (2006.01) |
| *A61B 17/72* | (2006.01) |
| *F03G 1/10* | (2006.01) |

(52) U.S. Cl.
CPC ............... *F03G 7/065* (2013.01); *A61B 17/66* (2013.01); *A61B 17/7216* (2013.01); *F03G 1/10* (2013.01)

(58) Field of Classification Search
CPC .. F03G 1/10; F03G 7/065; A61B 2017/00867
See application file for complete search history.

(56) References Cited

U.S. PATENT DOCUMENTS

| | | |
|---|---|---|
| 5,415,660 A | 5/1995 | Campbell et al. |
| 6,730,087 B1 | 5/2004 | Butsch |
| 2003/0032958 A1 | 2/2003 | Soubeiran |
| 2009/0013684 A1 | 1/2009 | Takahashi |
| 2009/0076597 A1 | 3/2009 | Dahlgren et al. |
| 2009/0302708 A1* | 12/2009 | Takahashi ............... F03G 7/065 310/306 |

FOREIGN PATENT DOCUMENTS

| | | |
|---|---|---|
| DE | 10 2007 036 359 | 2/2009 |
| EP | 0 919 717 A1 | 6/1999 |
| EP | 2 133 566 A2 | 12/2009 |
| FR | 2 726 460 | 5/1996 |
| JP | 2002-519136 A | 7/2002 |

(Continued)

OTHER PUBLICATIONS

Finnish Communication of Acceptance (Patent Application No. 20135175) (2 pages—dated Nov. 24, 2014).

(Continued)

*Primary Examiner* — Jonathan Matthias
(74) *Attorney, Agent, or Firm* — Renner, Kenner, Greive, Bobak, Taylor & Weber

(57) ABSTRACT

The present invention is about an actuator comprising at least one shape-memory-alloy based converter in a housing and at least one preload spring. The actuator is configured to cause a motion of at least one movable member. The optimal structures along with corresponding methods for improving an actuator are claimed in the independent claims. Preferable embodiments are presented in the dependent claims.

12 Claims, 17 Drawing Sheets

(56) References Cited

FOREIGN PATENT DOCUMENTS

WO       02/094113 A1   11/2002
WO   2009/115645 A1   9/2009

OTHER PUBLICATIONS

Finnish Office Action (Patent Application No. 20135175) (4 pages—dated Oct. 2, 2013).
Finnish Search Report (Patent Application No. 20135175) (2 pages—dated Oct. 2, 2013).
Japanese Office Action with English Translation (Application No. 2015-558519) (8 pages—dated Dec. 19, 2017).

* cited by examiner

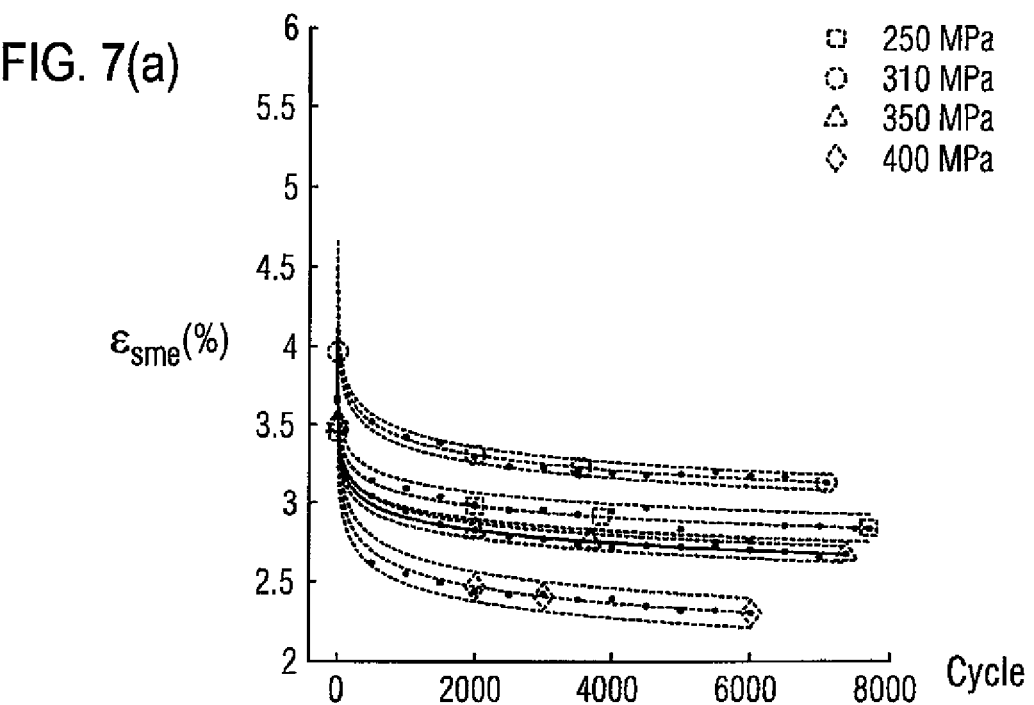
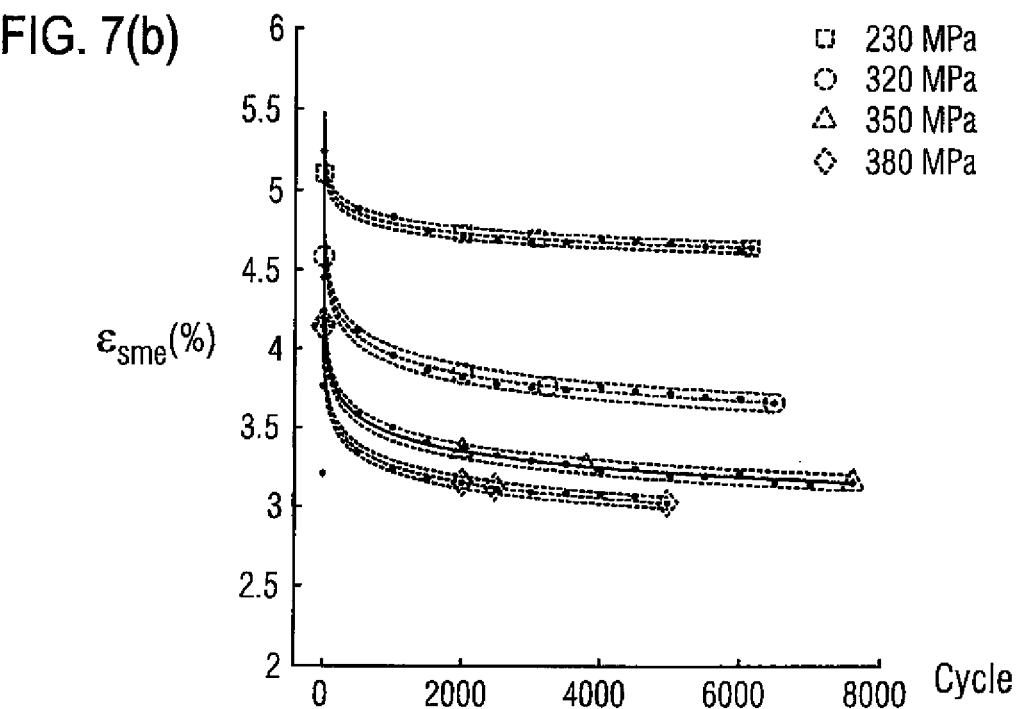

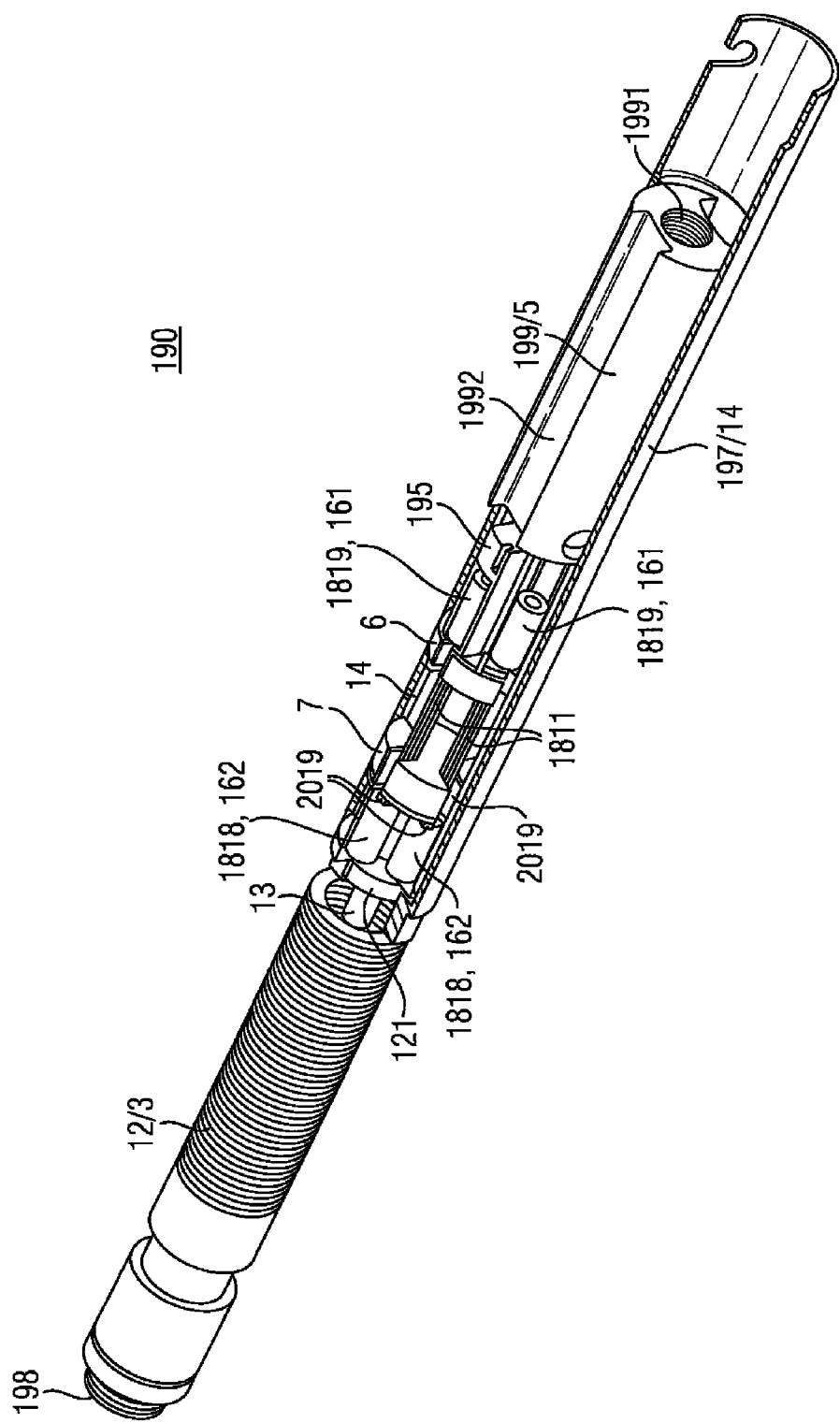

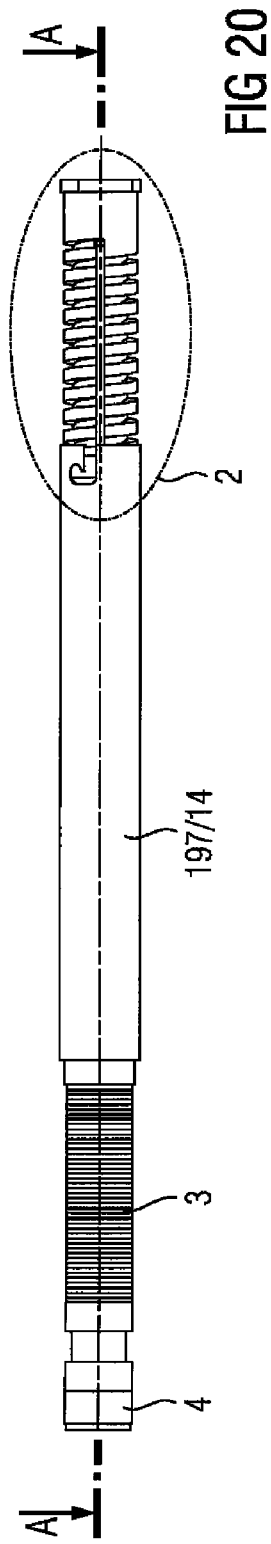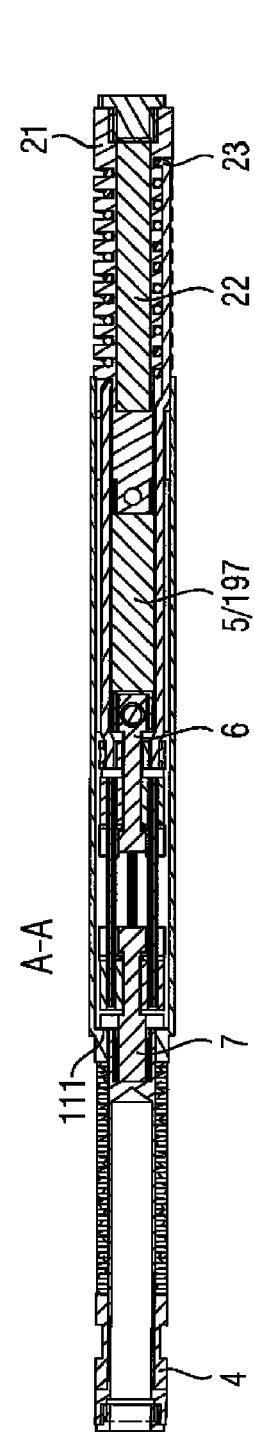

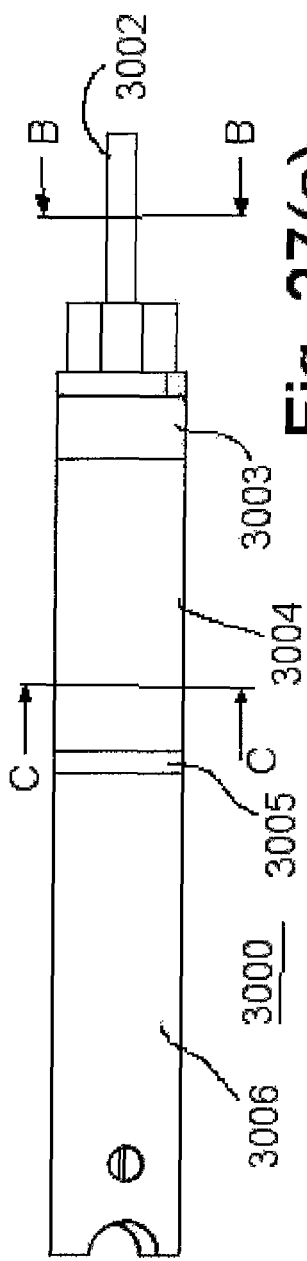
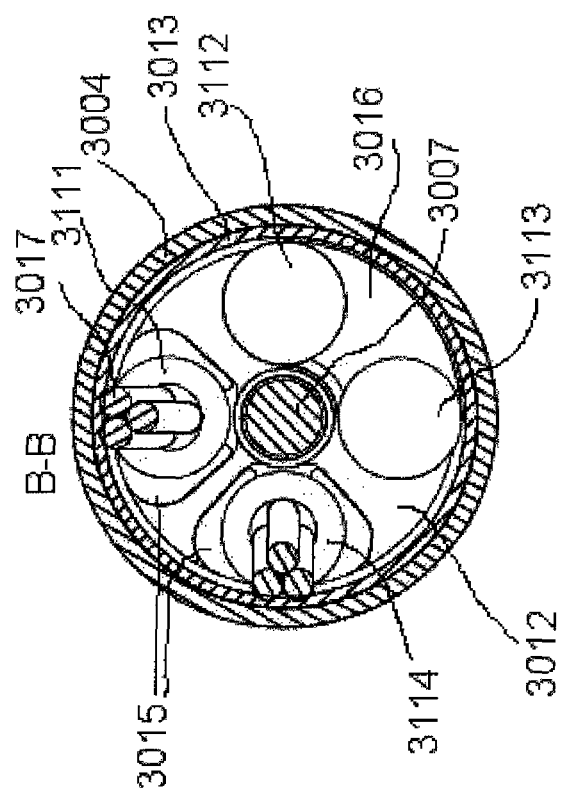
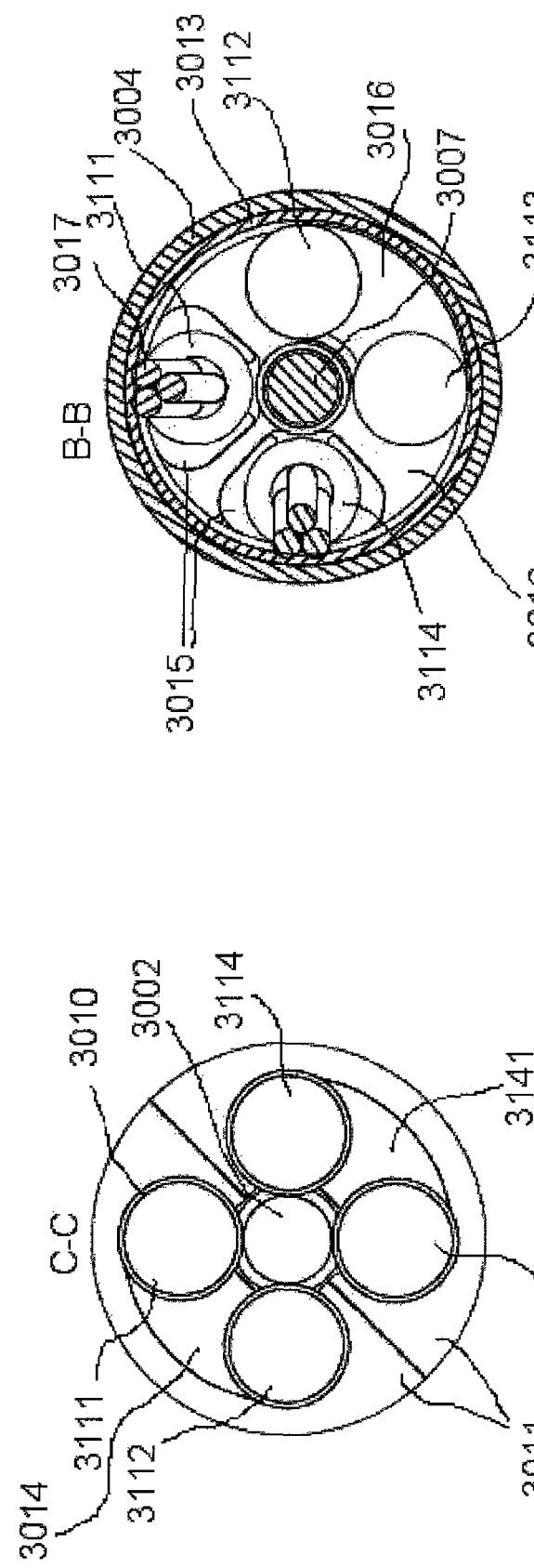
Fig. 27(a)
Fig. 27(b)
Fig. 27(c)

ACTUATOR AND METHOD FOR IMPROVING AN ACTUATOR

CROSS-REFERENCE TO RELATED APPLICATION

This application is a continuation of U.S. patent application Ser. No. 14/767,106 filed on Aug. 11, 2015, which is incorporated herein by reference, which was, based upon and claimed the benefit of priority from the prior PCT/FI2014/050119 filed on Feb. 18, 2014; and Finnish Patent Application No. FI 20135175, filed on Feb. 22, 2013, the entire contents of which are incorporated herein by reference.

PUBLIC FUNDING NOTICE

This document may contain results from work funded by Tekes (The Finnish Funding Agency for Technology and Innovation), Aalto University, and Orton Foundation.

FIELD OF THE INVENTION

The invention relates to construction and use of shape-memory-alloy based actuators.

BACKGROUND ART

Actuators utilizing shape change of shape memory alloys or magnetostrictive materials are known from published patent applications WO 2009/115645 A1 and WO 2011/148047 A1.

OBJECTIVE OF THE INVENTION

It is an objective to improve actuators utilizing shape change of shape memory alloys.

This objective can be fulfilled with an actuator according to claim 1, and with the method according to claim 7.

The dependent claims describe various advantageous aspects of the actuators.

Advantages of the Invention

Actuator according to the invention comprises at least one shape-memory-alloy based converter in a housing and at least one preload spring. The actuator is configured to cause a motion of at least one movable member in a first direction, upon the at least one converter undergoing thermally induced phase transition which makes it contracted, and in a second direction that is opposite to the first direction, upon the at least one converter undergoing phase transition caused by temperature change and enhanced by the preload spring which makes the converter elongated.

Furthermore, the actuator comprises at least one restrictor configured to restrict the strain of the at least one converter caused by the preload spring. In the actuator, the at least one preload spring in its initial state is preloaded with a preloading force and configured to cause the at least one converter in its resting state a tensile force that is limited by the at least one restrictor in such a manner that the tensile force resulting from the tension in the at least one converter is smaller than the force exerted by the at least one preload spring to the converter during phase transition.

The actuator of the invention is characterized in that the at least one converter comprises at least one bundle of individual wires or rods made of or consisting shape-memory-alloy in such manner that in the bundle the individual wires are electrically connected to each other in series or in parallel and mechanically arranged in parallel.

According to a further aspect of the invention, an actuator comprises at least one shape-memory-alloy based converter configured to cause a motion of at least one movable member and located in a housing. Furthermore, the actuator comprises at least one preload spring that is configured to preload the at least one shape-memory-alloy based converter. The improvement comprises at least one restrictor that is configured to restrict strain of the at least one converter caused by the preload spring.

With the actuators as suggested, the force that can be exerted by the movable member during its movement in the second direction can be increased significantly as compared to the force that is obtainable by the actuator that has no preloading. More precisely, with our actuator, during the movement in the second direction, the force that can be exerted by the movable member is not any more the force of the at least one shape-memory-alloy based converter but the force of the at least one preload spring.

An advantage that may be obtainable with our actuators is that the amount of movement that can be caused by the actuator during the work phase can be made more predictable than in an actuator in which at least one shape-memory-alloy based converter and a preload spring but no restricting of the preload force exerted by the preload spring is employed, as suggested by our results shown in FIG. 6. This enables a much more simpler construction as compared with the one-degree-of-freedom positioning system proposed by Azfal Khan et al. in their poster SHAPE MEMORY ALLOY WIRES FOR ACTUATING POSITIONING SYSTEMS WITH ELASTIC BEARINGS, at the time of writing electronically retrievable under http://www.aspe.net/publications/Annual 2005/POSTERS/2EQUIP/3DTEST/1815.PDF.

A further advantage we consider potentially very relevant for certain uses is that our actuators may be capable for more cycles before failure. The main purpose of the restrictor is to avoid such a high preloading force to damage the at least one shape-memory-alloy based converter.

If the actuator further comprises at least one preloading compression-to-tension transformator connector for passing force exerted by the at least one preload spring to the converter, the configuration of the actuator can be carried out by a relatively simple mechanical structure.

As in the actuator the at least one converter comprises at least one bundle of individual wires or rods made of or consisting shape-memory-alloy in such a manner that in the bundle the individual wires are electrically connected to each other in series or in parallel and mechanically arranged in parallel, we can ensure that the contractive force obtainable from the at least one converter via its phase transition is high enough since arranging wires or rods in parallel sums the contractive force of each individual wire or rod together. Optionally, if there are more than one bundle, the bundles may be connected to each other electrically in series. In this manner, we can ensure that the heating of all wires or rods in the bundle can be carried out simultaneously in order to avoid damaging the actuator by non-uniform deformation that could result in bending of the actuator, for example. In addition, the bundles may preferably be connected in parallel to increase force or to achieve desired form of movement.

If the actuator further comprises at least two connectors electrically connected to said bundle for feeding electrical energy received from a power source, such as from a wirelessly switchable battery or through at least one inductive coil in said actuator to the bundle, the actuator can be used in a wireless manner. This is particularly important in such use situations of the actuator when the actuator is designed as an actuator of an orthopedic treatment device that is implemented in a patient for a treatment of several days, weeks or even months, since thanks to the wireless useability, the energy can be supplied in a wireless manner to the actuator and therefore the need to have open wounds in the patient during the treatment may be removed.

If in the actuator comprising at least one bundle of wires or rods, the electrical and mechanical connection between the individual wires of the bundle is implemented within at least one connecting unit and wherein the restrictor is configured to restrict the tensile force of the bundle by restricting the movement of the at least one connecting unit or a connection to force transmission in the work direction of the at least one preloading spring, the at least one connecting unit can be used to absorb much or even all of the difference to cut the higher preload stress of the preload spring to a lower force that acts as the tensile force on the at least one converter.

If in the actuator the preload spring is arranged around the converter in such a manner that contraction of the converter pulls the movable member compressing the preload spring, the actuator can be made smaller. Additionally to this, or as an alternative, it can be ensured in a relatively simple manner that the relative spatial location of the preload spring and converter to each other remains practically unchanged during the operation of the actuator.

If the housing of the actuator is encapsulated in a biocompatible material or consists of biocompatible material, the actuator can be used as an actuator in medical appliances or similar that may come into connection with bodily fluids or bodily tissues.

Preferably, the actuator is joined to a transformer transforming reciprocating motion of the movable member to a unidirectional motion. In this manner, the actuator can be used as the actuator of a device that converts the movement of the actuator to distracting movement (by extending movement or movement outwards) or to contracting movement (by shortening movement or movement outwards). Devices producing distracting or contracting movement are widely used in the field of medicine and in particular in orthopedics.

Preferably, the shape-memory-alloy based converter is or comprises one or more NiTi elements. Particularly advantageously, the stress imposed on some or all NiTi elements by the preloading force is in the range of 250-450 MPa during actuation and the tensile stress caused on the NiTi elements in it's martensite state is 20-90 MPa. In this manner we can ensure that the forces that can be produced by the actuator are high enough for many practical purposes, in particular in the field of orthopedics and in particular for osteodistraction or scoliosis treatment devices, such as but not limited to devices used in connection with mandible, metacarpals, metatarsals, cranial vault, mid-face, long tubular bones or other bones. Within the presented range of the preloading forces and tensile stress, the strain of the NiTi elements is with a high probability better predictable. In addition, the actuator may have an extended lifetime i.e. it can be used to undergo more cycles under load.

Preferably, the actuator is suitable for use as an actuator in an implantable treatment device fixed or interlinked to bone.

The actuator may in particular comprise a plurality (i.e. at least two) actuators assembled next to each other in the housing. This kind of configuration is in particular suitable for a scoliosis treatment device or an internal osteodistraction device.

Alternatively, the actuator may comprise a number of converters arranged around an axis. This kind of configuration is in particular suitable for a bone distraction actuator of an internal osteodistraction device.

Another actuator according to the invention comprises at least one shape-memory-alloy based converter in a housing and at least one preload spring. The actuator is configured to cause a motion of at least one movable member
  in a first direction, upon the at least one converter undergoing thermally induced phase transition which makes it contracted, and
  in a second direction that is opposite to the first direction, upon the at least one converter undergoing phase transition caused by temperature change and enhanced by the preload spring which makes the converter elongated.

Furthermore, the actuator comprises rod connecting to the said movable member and to a spring. The spring may be a compression spring stack placed around the spring compression rod. The spring may also be a tension spring connecting to the end of the rod. In the actuator, the rod is pulled to the optimal prestress for the converter such that a fixation part can be added. The added fixation part holds the optimal prestress.

The same embodiments as for the previous actuator can be utilized for this another actuator.

LIST OF DRAWINGS

In the following, the actuators are described in more detail by reference to the examples shown in the attached drawings in FIGS. 1 to 28, in which.

Figure 1:
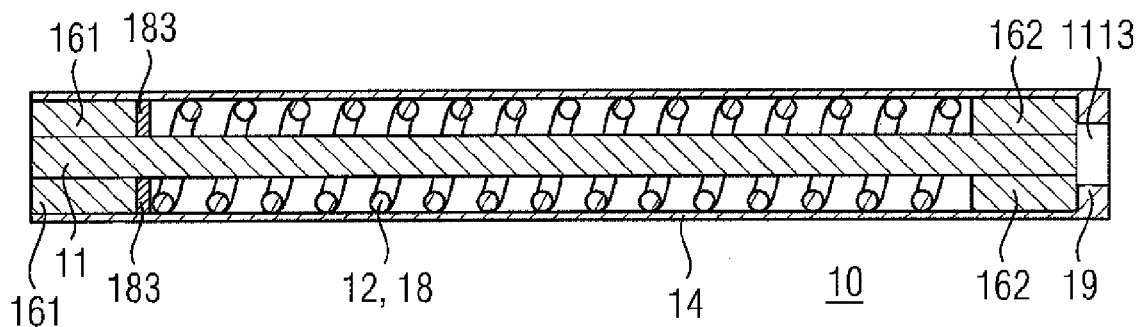
FIG. 1 illustrates the concept of actuator based on the testing system presented.
Figure 3:
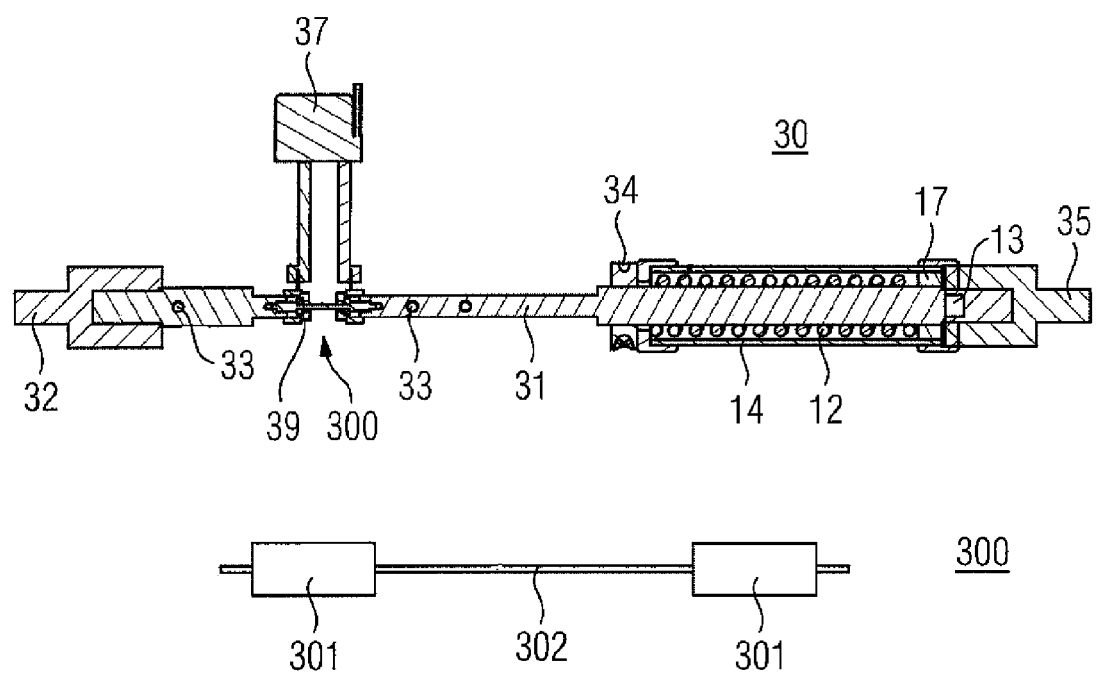
Figure 4A:
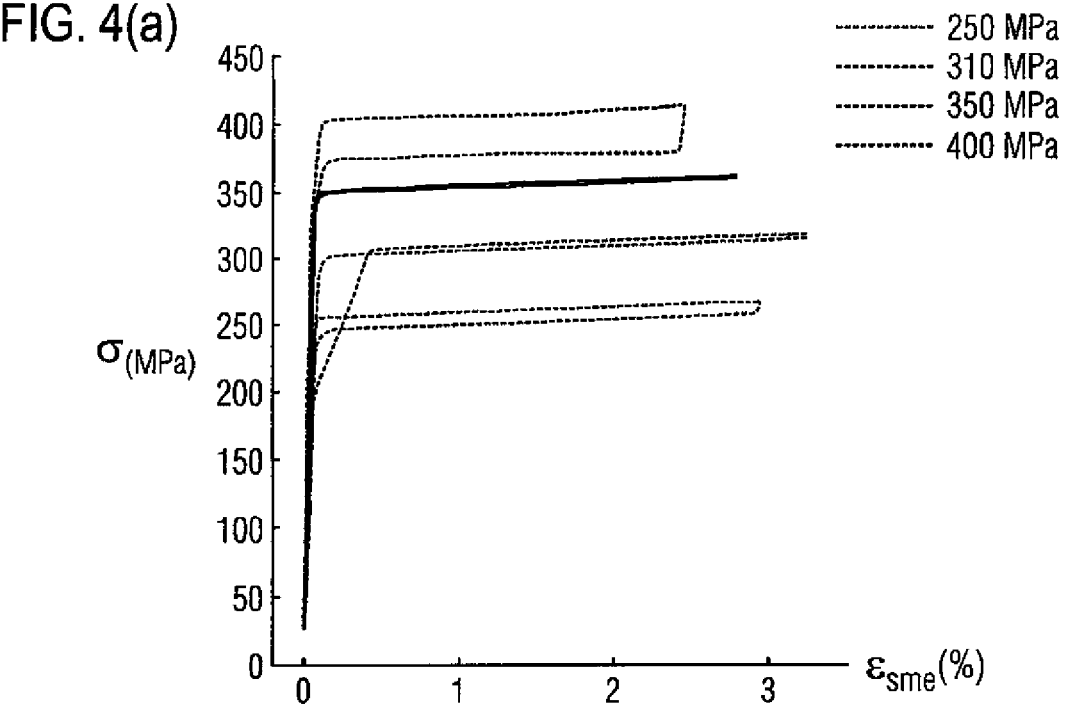
Figure 4B:
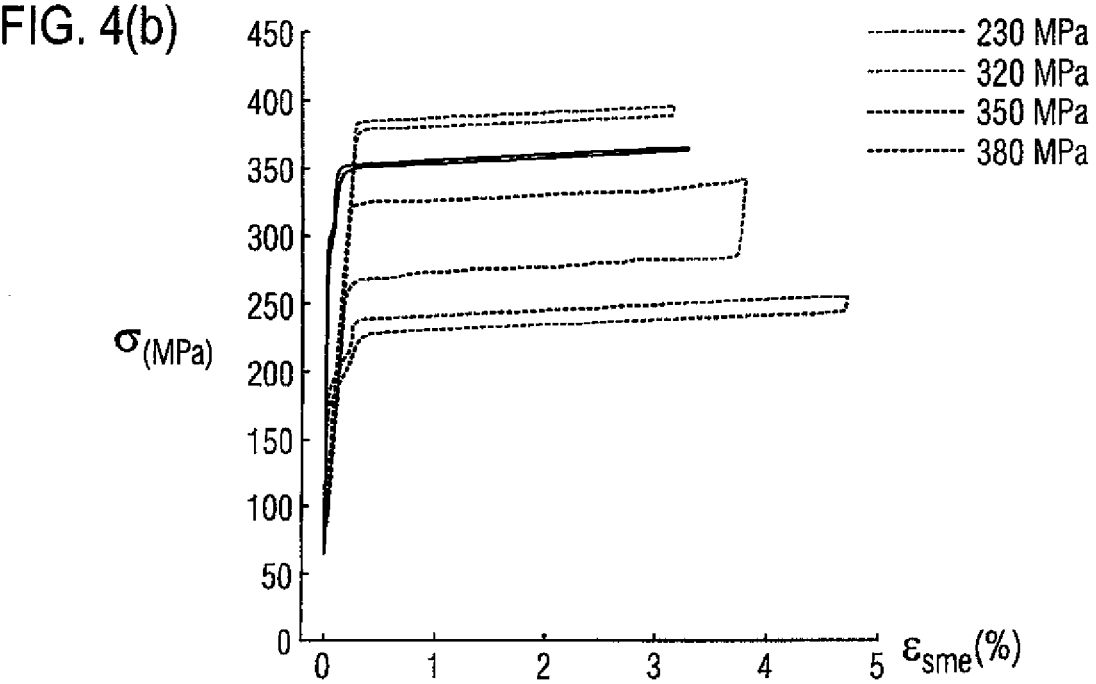
Figure 5:
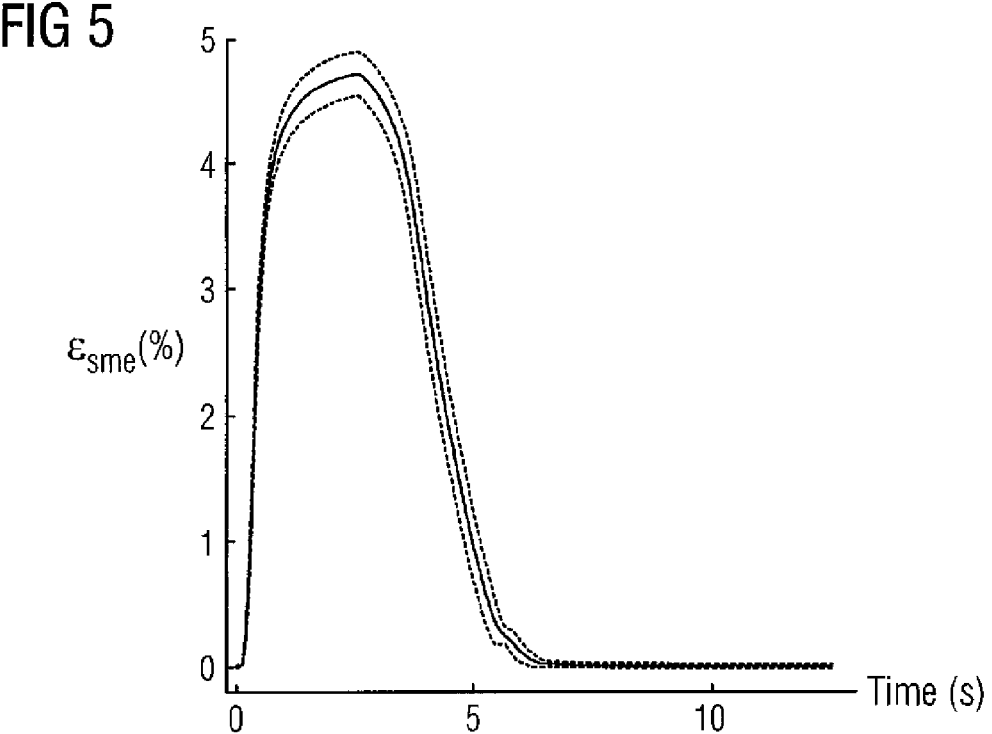
Figure 6:
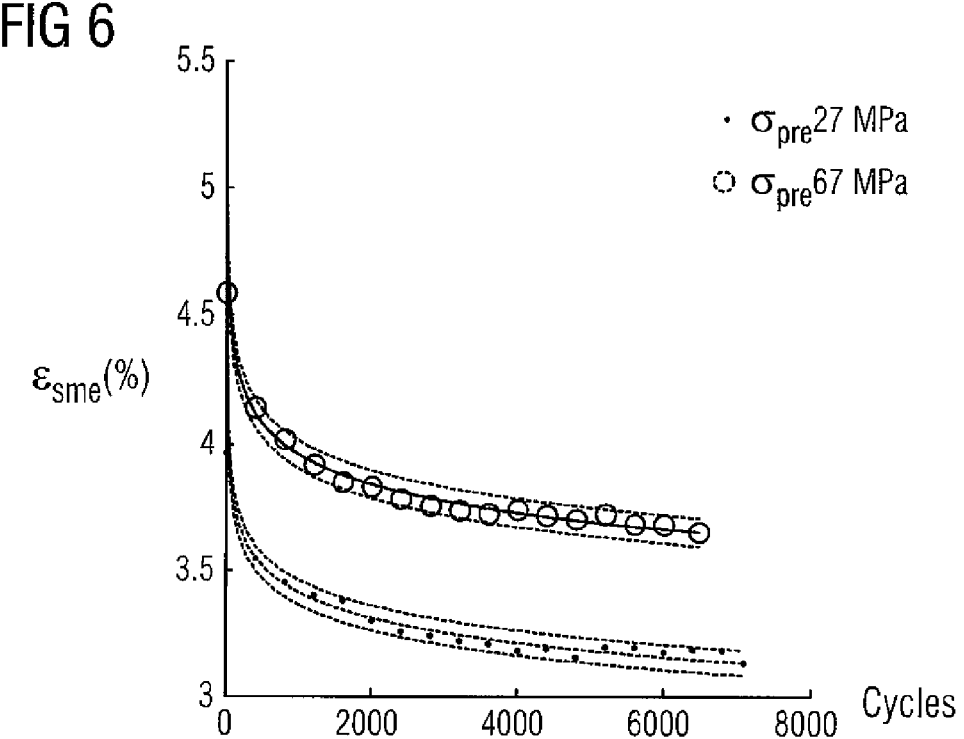
Figure 9:
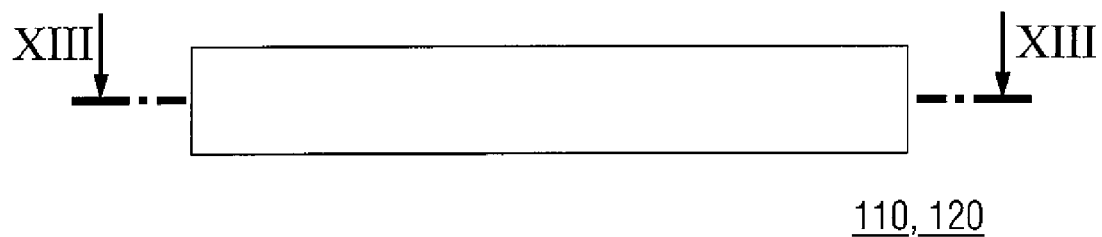
Figure 10:
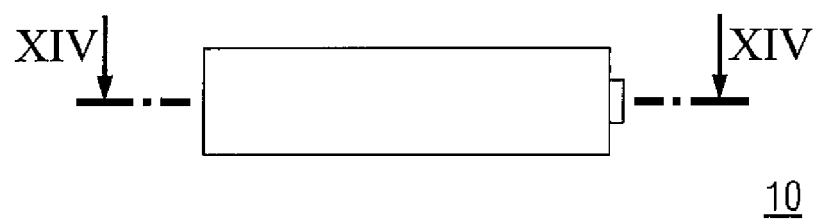
Figure 11:
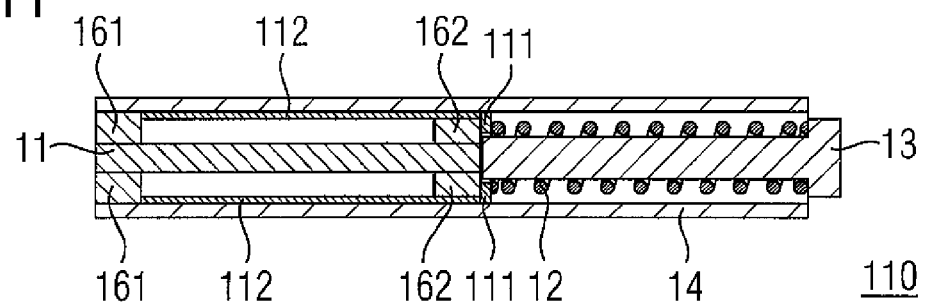
Figure 12:
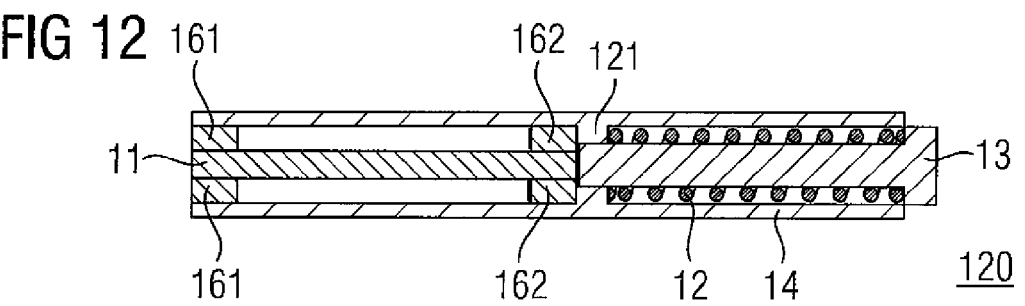
Figure 13:
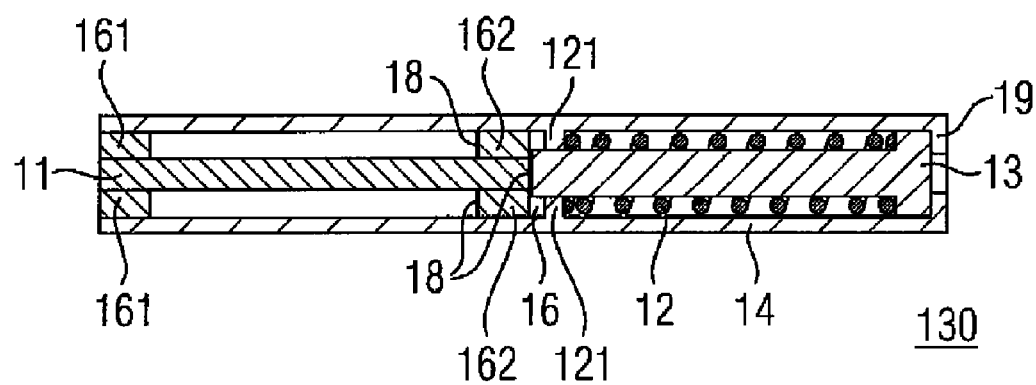
Figure 14:
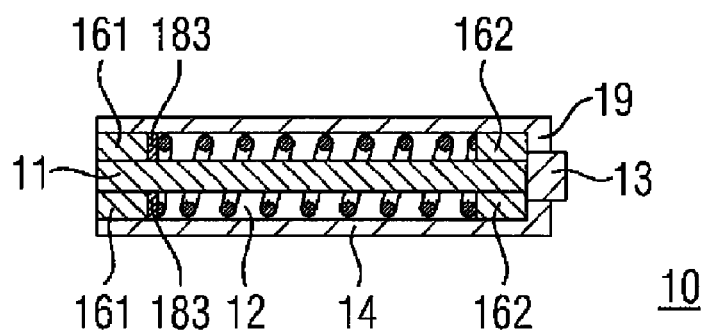
Figure 15:
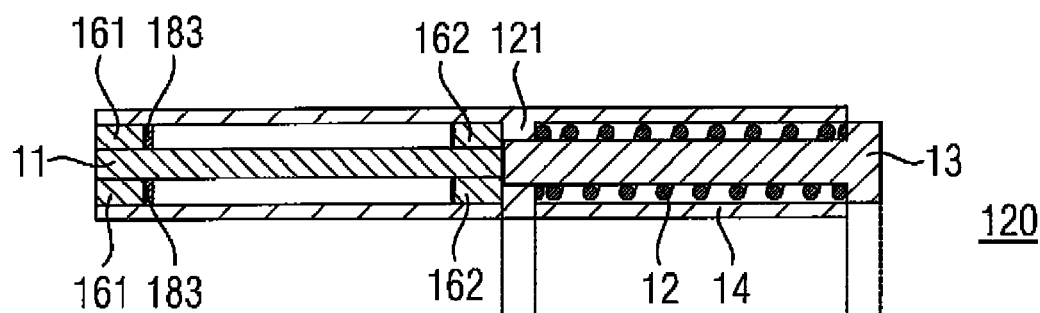
Figure 16:
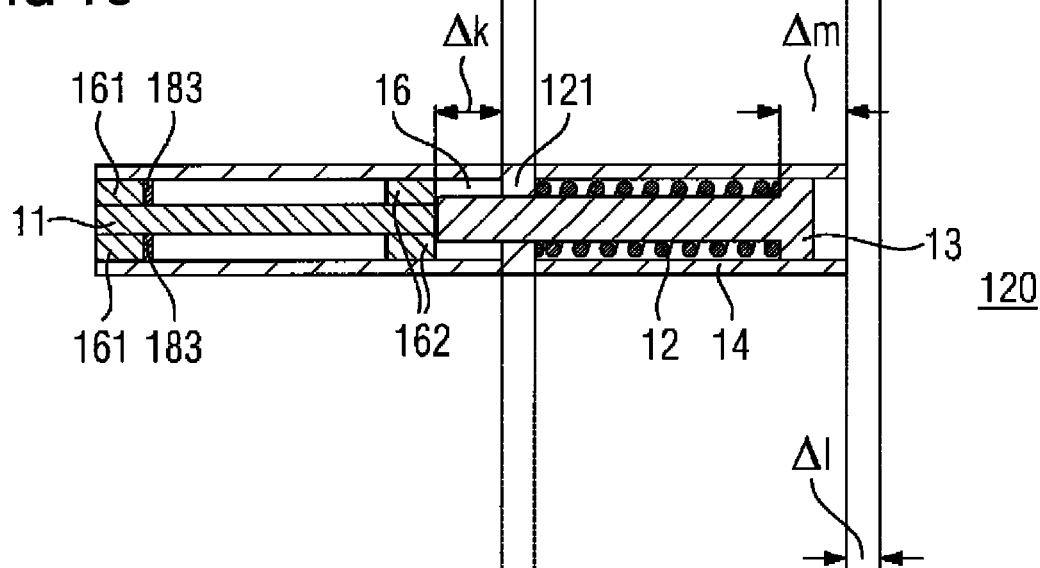
Figure 17:
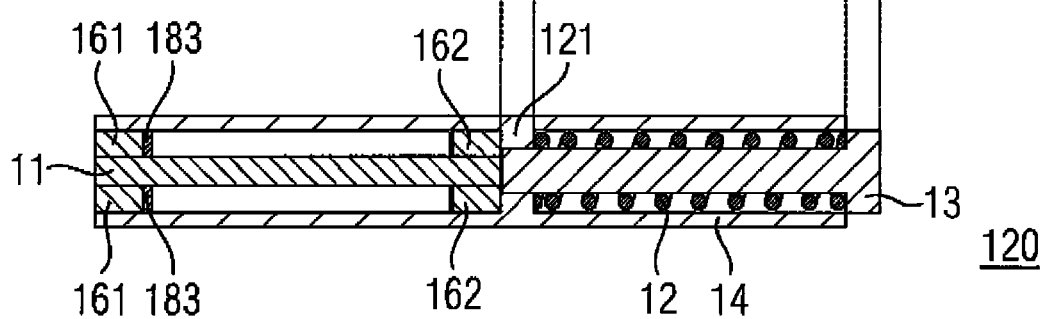
Figure 18:
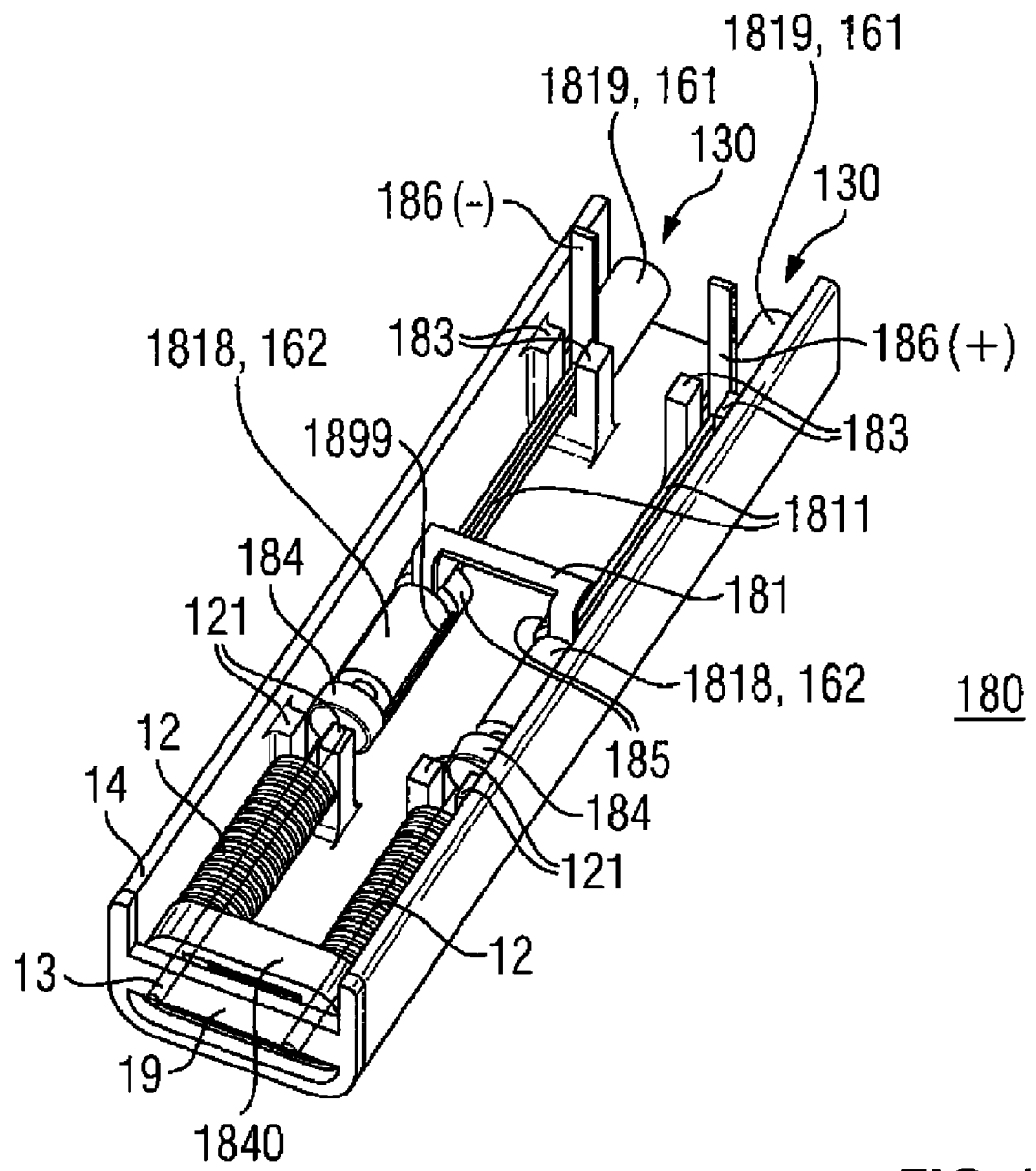
Figure 22:
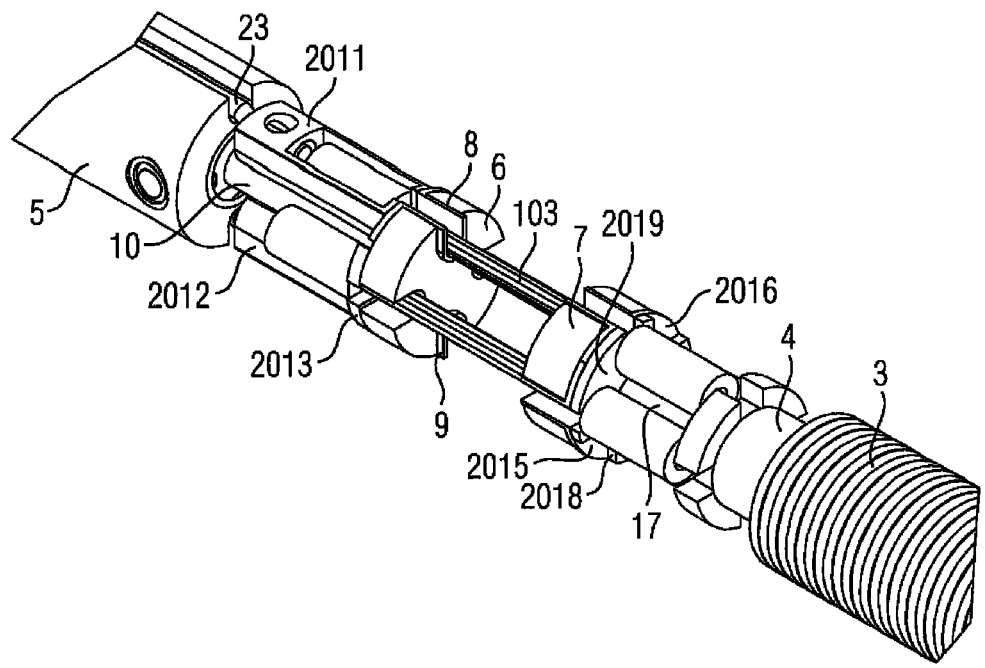
Figure 23:
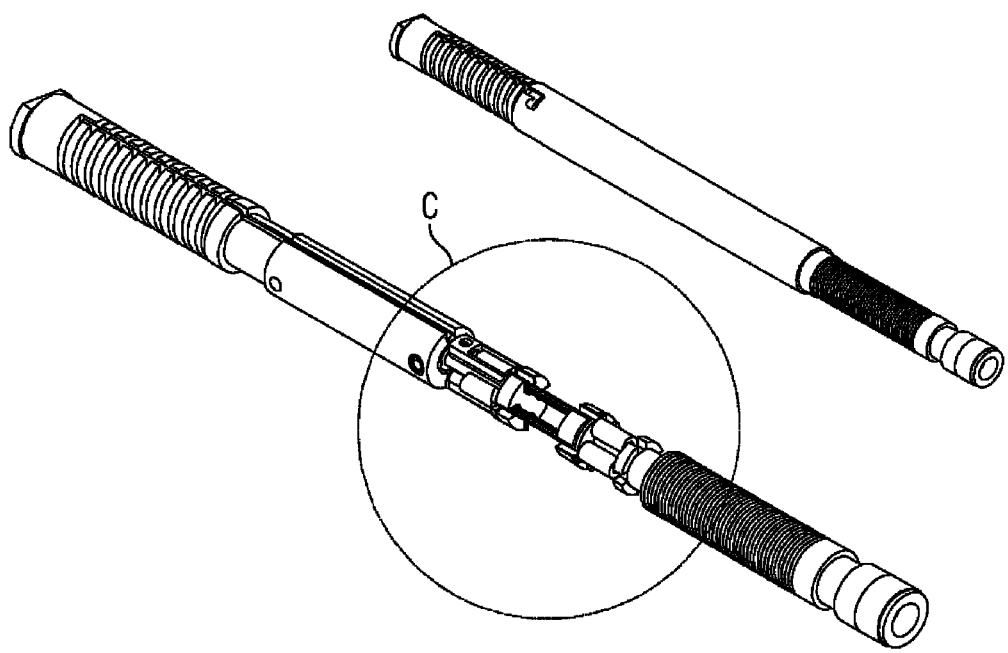
Figure 24:
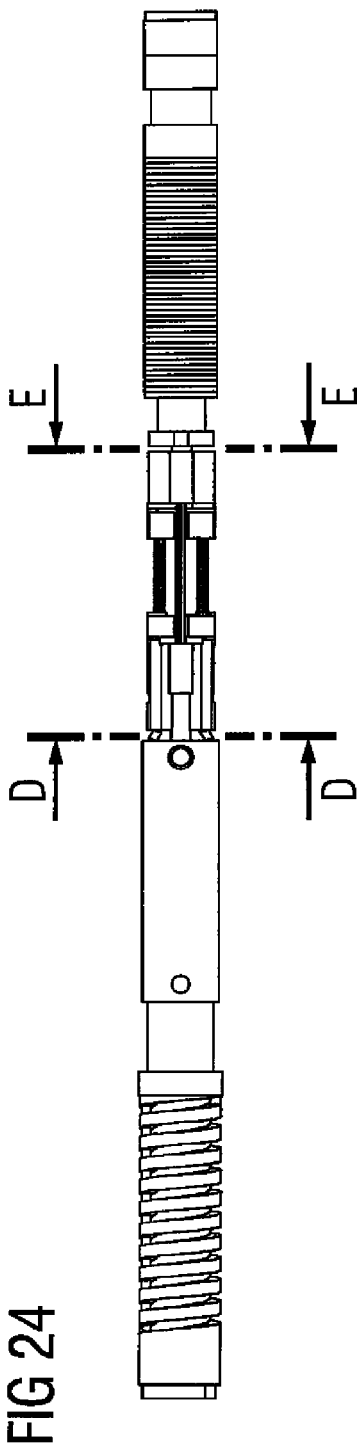
Figure 25:
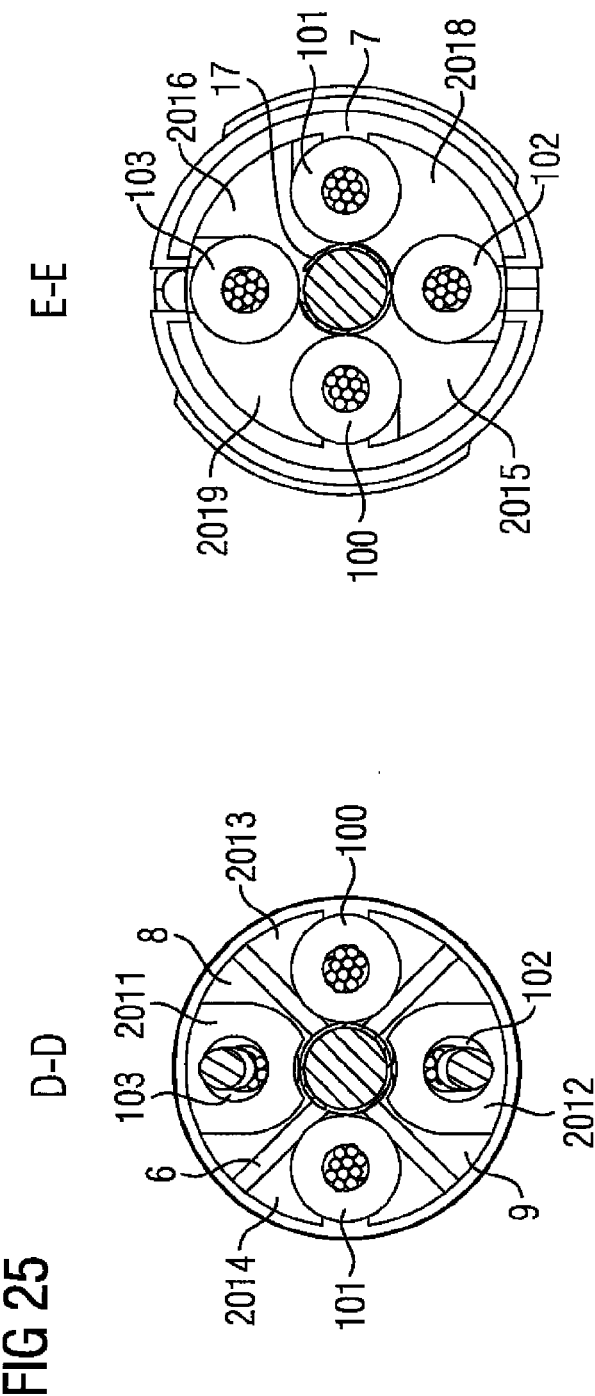

FIG. 3 schematic of the testing system and the samples used;

FIGS. 4(*a*) and (*b*) illustrate the stress-strain behaviour of the NiTi wire in the test system, (a) shows the test at 30 MPa and (b) the test at 69 MPa, the higher stress level on each curve is recorded during heating and the lower level during cooling;

FIG. 5 illustrates strain behaviour of NiTi during actuation at a prestress of 69 MPa and stress level of 250 MPa, the solid line is the mean of the actuation cycles of the test and the dotted represent standard deviations of the test;

FIG. 6 illustrates the strain versus cycle number under a load of 300 MPa;

FIGS. 7(*a*) and (*b*) illustrate the strain behaviour of the NiTi elements under different load conditions: (a) shows the performance under a prestress of 30 MPa and (b) under a prestress of 69 MPa;

FIGS. 8(*a*) and (*b*) in (a) is the achieved net stress illustrated as a function of the achieved strain and in (b) the achieved net stress is illustrated as a function of the achieved fatigue life for all of the tested stress-prestress combinations: the black symbols denote a prestress of 69 MPa and the open symbols a prestress of 30 MPa;

FIG. 9 schematic drawing of a second embodiment of the actuator presented;

FIG. 10 schematic drawing of the first embodiment of the actuator presented in FIG. 1;

FIG. 11 a section of a first actuator according to the second embodiment;

FIG. 12 a section of a second actuator according to the second embodiment;

FIG. 13 a section of a second actuator according to the second embodiment in a contracted state;

FIG. 14 a section the actuator according to the first embodiment shown in FIGS. 1 and 10;

FIGS. 15-17 illustrate the cycle of an actuator according to the second embodiment, from initial phase of the actuator, through movement in the first direction to the contracted phase and through movement in the second direction back to the initial phase;

FIG. 18 illustrates certain components of an actuator according to a third embodiment that is an actuator that comprises at least two actuators assembled next to each other in the housing;

FIG. 19 illustrates certain components of an actuator according to a fourth embodiment that is an actuator that comprises a number of converters arranged around an axis;

FIGS. 20, 23 and 24 illustrate a bone distraction actuator;

FIG. 21 section A-A of the bone distraction actuator;

FIG. 22 is a zoomed view C of spring stack end of the bone distraction actuator as illustrated in FIG. 23; and FIG. 25 illustrates sections D-D and E-E at locations illustrated in FIG. 24.

Figure 26:
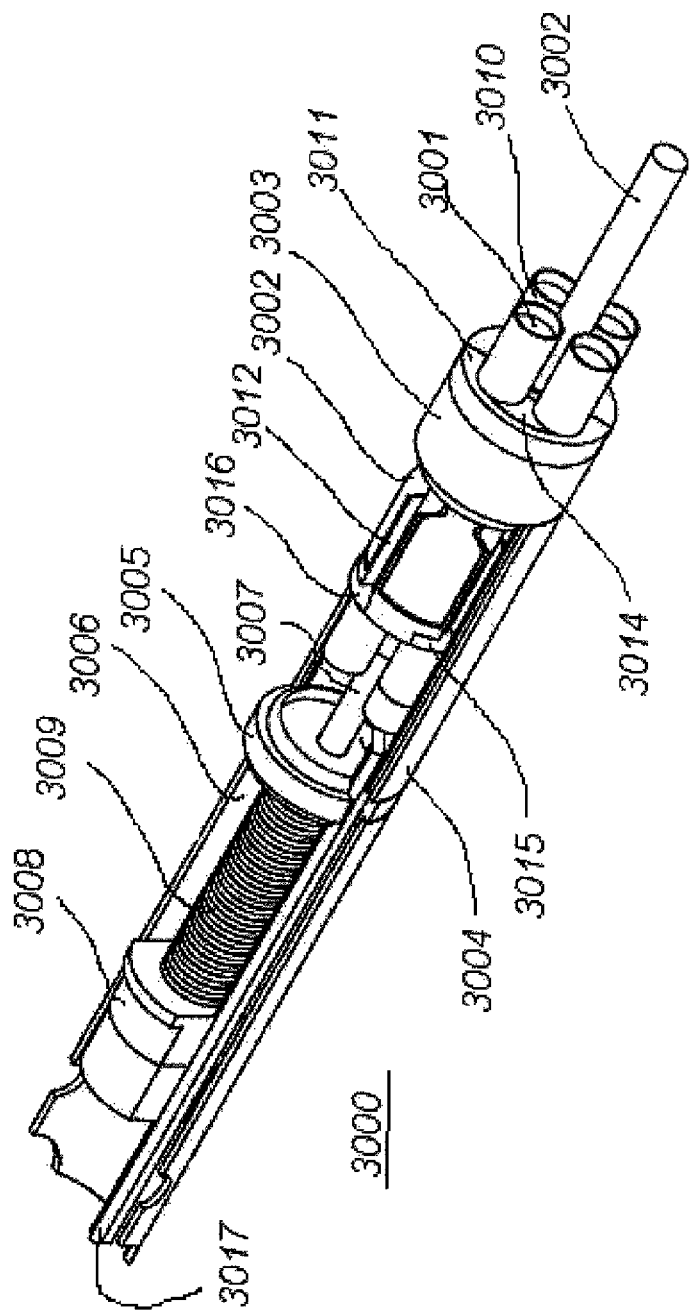

FIG. 26 illustrates the parts of the actuator

FIG. 27 (a) illustrates general view of the actuator

FIGS. 27 (b) and (c) illustrate the section views of the critical points of the actuator of FIG. 27 (a).

Figure 28:
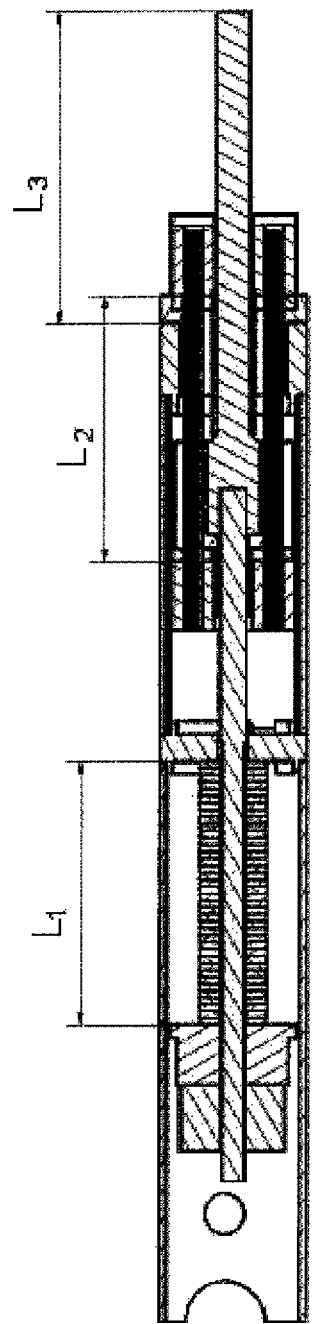

FIG. 28 illustrates the positions of the actuator parts

The same reference numerals refer to the same technical features in all drawings.

DETAILED DESCRIPTION

1. Introduction

We have invented a shape memory alloy (SMA) actuator that produces a predictable output performance and tested it.

There are several application areas for SMA actuators with tight space limitations, where the control of the actuator by utilizing sensors is difficult to realize.

The test system for the actuator concept allowed the performance evaluation of NiTi against a constant load with different prestresses. Commercially available NiTi elements, Flexinol® (trade mark of Dynalloy, Inc.) wires, were tested in this system against high constant load levels of 250, 300, 350 and 400 MPa at two different prestress values 30 MPa and 69 MPa. The strain output and fatigue life of the NiTi wires under these conditions were measured. Increasing the stress level was found to decrease the fatigue life as expected. In addition, increasing the prestress from 30 MPa to 69 MPa improved the strain output at all stress levels. We found out that different stress-prestress combinations can lead to the same net output force from the material but their maximum strain output and fatigue life are different. According to the results, the actuator concept is feasible and can be realized with predictable output performance.

Shape memory alloys are used in a wide variety of applications ranging from medical devices and implants (Aalsma 1997, Ryhanen 1999) to aerospace applications (Chau 2006) and robotics (Kheirikhah 2011). Most of these applications utilize binary nickel-titanium alloys because of their superior mechanical and shape memory properties.

Generally, in typical actuator applications, nickel-titanium (NiTi) elements are designed to last for hundreds of thousands of cycles, which in turn limit the stress level to under 200 MPa (Dynalloy 2012, Mertmann 2009).

Fumagalli et al. (2009) presented the common reset mechanisms used in SMA actuator applications. In all of these reset mechanisms, the NiTi element works directly against the external load. Similar designs have been proposed by others (Aalsma 1998, Elwaleed 2007, Kim 2008). However the strain and fatigue life performance of NiTi has been shown to depend greatly on the stress imposed on it (Lagoudas 2009, Mammano and Dragoni 2012, Bertacchini 2009). This leads to unpredictable actuation behaviour, and accurate control requires sensors and feedback loops.

NiTi alloys are particularly lucrative for use in medical implants due to their established biocompatibility (Ryhänen 1999, Shabalovskaya 2002) and high power density (Reynaerts 1998). In many of these applications, for example in the field of orthopaedics, large forces are needed but the space is limited.

The space limitations also limit the possibility of using sensors for actuation control. Therefore, it would be a great advantage if an actuator could be constructed in such a way that behaves predictably under various loading conditions. In addition, the amount of actuation cycles needed in orthopaedic applications are usually fairly low. This allows the utilization of SMAs at high stress levels, which has not been extensively studied.

Shape memory alloys are also introduced in Dahlgren 2009. In the application, the NiTi elements are movable on each pulse and change their position in the implant. This means that the external load exerted on the NiTi elements is not well known and will change according to the location of the elements.

Additionally, a device for moving two bodies relative to each other is presented in Soubeiran 2003. The application utilizes a spring. The power of the device is reduced by increasing the number of actuations, as the compression of the spring decreases. This would, in practice, lead to the device to become stuck. It doesn't give any hint about utilizing the shape memory alloys or any other intelligent materials.

Helsinki University of Technology 2009 introduces the shape memory alloy but not the application of it. In the application, the spring is only the preload spring of the magnetostrictive material and it does not apply any external work.

Further, the publication Olympus Corp. 2012 introduces an actuator that a shape memory alloy wire, that contracts when heated and expands when cooled. The device consists of a hollow member, a movable element, an elastic member and an insulation member. The shape memory alloy wire is prevented from being in electrical contact with the elastic member. Thereby, the NiTi element is isolated from the preload spring. However, the isolation members also carry the load, which in practice would cause problems as the typical materials are not strong enough.

Takahashi M 2009 describes a generic SMA-actuator, which allows reciprocal movement of the movable member by the amount of the lengthening capacity of the SMA-element.

Stolz-Irion R 2009 describes an elongating intramedullary nail using SMA actuator to perform the gradual lengthening of the device.

In this communication, an actuator concept that utilizes NiTi in generating a predictable strain and force output is presented. The concept is evaluated using a testing system that simulates the behaviour of NiTi in loading conditions similar to that of the proposed actuator. The performance of the NiTi actuator wires is evaluated under various high stress levels with two different prestress values. Particularly the evolution of the strain in the martensitic and austenitic phase and the fatigue life of the material are studied. These results can be utilized to realize the proposed actuator concept and to optimize it for various stress levels.

It is still another advantage of the present actuator concept, that the NiTi elements stay in one position inside the implant, and thereby, the external loads can be minimized because the knowledge of the exact position can be used to direct the loads, e.g. bending, away from this area. The advantages are gained by stabilizing the external work of the device, by utilizing small isolative members that are free of loads.

Horst et. al. 2013 discusses the medical device including an artificial contractile structure having at least two contractile elements adapted to contract an organ. The NiTi element of the publication is used for squeezing a tubular body part. The publication does not give any hint about separating the ends of the NiTi element such that the compression of the NiTi element would cause device pats diverging from each other.

Belson 2013 discusses an apparatus an a method for endoscopic colectomy. The publication does not give any hint for utilizing a preload spring or transferring its load to a NiTi element. The NiTi element is used for turning around the endoscopic end of the device. It does not give any hint for diverging device parts from each other.

It is an advantage of the another actuator of the invention that the NiTi elements can be used for separating or diverging the device parts from each other.

2. Materials and Methods

2.1. Actuator Concept

A schematic representation of actuator 10 that actuates against a constant and known load is presented in FIG. 1. The actuator comprises a NiTi element, a spring, and the housing (a tube, for example). The spring is preloaded to the stress level that the actuator is expected to produce. The NiTi element has to be fitted into the tube in such a way that its elongation in the martensitic phase causes the desired prestress to be exerted on it. Now when the NiTi element starts to elongate it will do work against the predetermined spring load. When the NiTi is allowed to cool, the spring returns it to the original position while a net force output is generated. The net force output can be defined as, $$F_{net} = (\sigma_s - \sigma_p) A \quad (1)$$

where $\sigma_s$ is the stress imposed on the NiTi by the spring when actuating, $\sigma_p$ is the stress acting on the NiTi in the martensitic phase, and A is the area of the NiTi element.

The required martensitic strain to cause the desired prestress in the NiTi element can be determined by using Hookes law, $$\epsilon_M = \sigma_p / E \quad (2)$$

where $\epsilon_M$ is the strain required to cause the prestress and E is the Young's modulus of NiTi in the martensitic phase. The shape memory strain of the actuator is calculated from the martensitic strain, $\epsilon_M$, and austenitic strain, $\epsilon A$. The shape memory strain is $$\epsilon_{SME} = \epsilon_M - \epsilon_A \quad (3)$$

Figure 2:
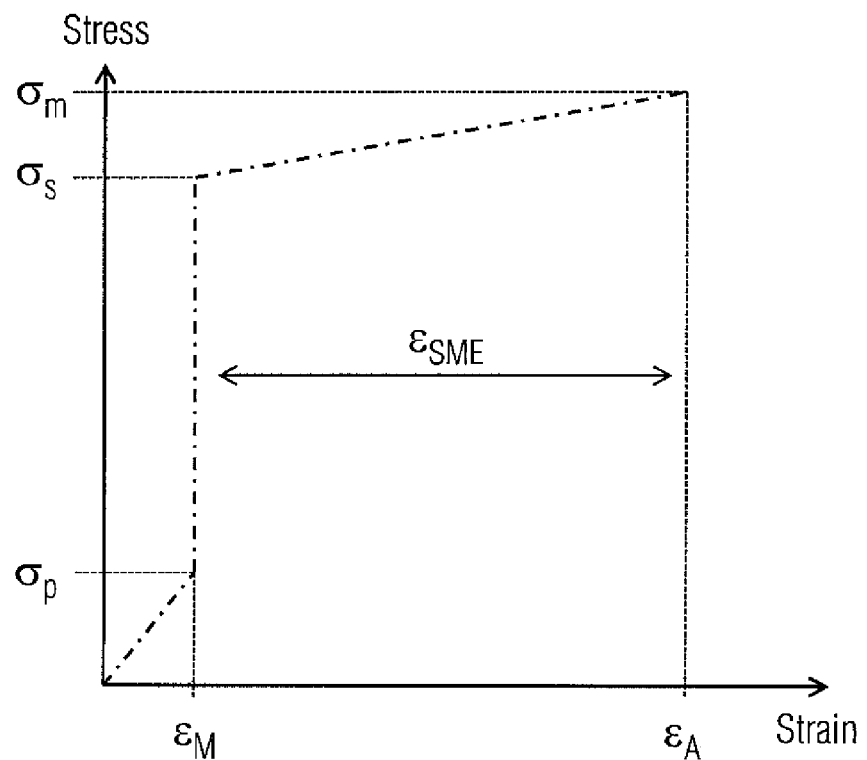
FIG. 2 illustrates theoretical stress—strain behaviour of actuator.

The theoretical stress-strain output of actuator 10 is shown in FIG. 2. When actuator 10 is being assembled, the strain in the martensitic phase is determined by Equation (2). When actuator 10 starts to actuate, the stress jumps straight to the stress level $\sigma_s$. At this point actuator 10 starts to generate a strain output, and the maximum stress $\sigma_m$ at least one NiTi element 11 works against, is determined by the preloaded stress of preload spring 12 and its spring factor k:

$$\sigma_m = \sigma_s + k \epsilon_{SME} / A \quad (4)$$

Once the at least one NiTi element 11 is allowed to cool, the energy stored in the preload spring 12 during heating is released and strain and force are generated from actuator output that is configured as movable member 13 (cf. FIG. 14) and/or that can be transmitted through opening 1113 for movable member.

An advantage of an actuator 10 is that the at least one NiTi element 11 always actuates against a known load. As long as the load defined by preload spring 12 selected is not exceeded, actuator 10 performs in a predictable way. However, because the prestress exerted on the at least one NiTi element 11 is determined by the attachment of the at least one NiTi element 11 in the actuator 10, it is important to know the evolution of the plastic strain in the martensitic phase. If an excess amount of plastic strain accumulates, the prestress imposed on the element changes and leads into changes in performance.

2.2. Evaluation of the Actuator Concept

In order to evaluate the feasibility of the actuator concept, a testing system 30 was designed and built. The NiTi wires 302 used were commercial grade Flexinol® acquired from Dynalloy, Inc. The nominal diameter of the NiTi wires 302 was 0.381 mm. The ends of the NiTi wires 302 were press-fitted with stainless steel barrel crimps 301 to allow easy mounting to the testing system. The length of the NiTi wire 302 between the crimps 301 was set to 20.0±0.1 mm. A schematic illustration of sample 300 is shown in the lower part of FIG. 3.

The test system 30 is shown in FIG. 3. The right side shows preload spring 12, having a small spring constant, inside housing 14 (preferably implemented as stainless steel tube). Rod 31 goes through preload spring 12 and is attached to sample 300, as shown on the left in FIG. 3. The other end of rod 31 is attached to steel block 17 that compresses the spring against the left side of the housing 14. Prior to attaching sample 300 to test system 30, the preload spring 12 was tightened to the desired level by using a material testing machine (MTS® 858 Table Top System, equipped with FlexTest® controller and MTS TestSuite™ Multi Purpose Elite software, all trade marks of MTS Systems Corporation). At the desired stress level, the preload spring 12 locking clamp 34 was tightened in place to hold the preload spring 12 at the load. In this way, the NiTi wire 302 was subjected to the full stress as soon as it started actuating as in the proposed actuator concept.

After the preloading of the spring, the NiTi wire 302 was attached to the preload spring 12 compression rod 31. At this point, sample 300 holding block 39 shown on the left in FIG. 3 was attached to the load cell connection 32 of the material testing machine and the load cell value zeroed. After the zero adjustment of the load cell, the sample 300 was attached to sample holding block 39 and the extensometer 37 was secured in place to record the strain.

Electric current was used to resistively heat the NiTi wire 302. Prior to activation of the current, the NiTi wire 302 was prestressed to a desired prestress value by using the hydraulic actuator of the material testing machine via the connection 35 to the hydraulic machine, to pull the NiTi wire 302. After the desired prestress value was achieved, the hydraulic actuator was held in place in displacement control mode while the current was applied and NiTi wire 302 started to actuate against the load of preload spring 12.

Actuation was achieved by supplying an electric current of 2.25 to 3.5 A for a duration of 2.25 to 5 seconds to NiTi wire 302. This was achieved using a power source in current limited voltage control mode, which was coupled to the NiTi wire 302 through a solid-state-relay. The operation of this relay was controlled by a program built for material testing machine. The optimal current and actuation time were selected in order to achieve as complete a transformation as possible into the austenite phase. This was done by observing the strain behaviour of the NiTi wire 302; and as soon as the strain started levelling to saturation, the current was switched off. No direct measurement of the temperature of the NiTi wire 302 was conducted. After the actuation, the samples 300 were cooled down by using forced air convection. This cycle of prestress-actuation-cooling was repeated until the samples failed.

Full force and strain data were recorded at 102.4 Hz from every tenth cycle. The maximum and minimum values of force and strain were collected from the remaining cycles. The strain was not corrected for strain caused by the stress or by the thermal expansion due to their limited effect compared to the shape memory effect.

3. Results

FIG. 4 shows stress-strain curves for NiTi wire 302 samples at different stress and prestress levels. It is evident that the test setup behaves as desired and NiTi wire 302 sample is subjected to the full stress almost immediately at the start of the actuation. However the raise in the stress is not instantaneous, as shown in the theoretical performance shown in FIG. 2. This is due to the spring locking clamp 34 also acting as a spring, although with a very high spring coefficient. As expected, the stress level is not fully constant during actuation, but rather increases according to the spring constant of the load spring, as described in Equation 4. The area inside the stress-strain loop at the top in FIG. 4(a) shows that there is some friction in the test system that causes the stress level during heating and cooling to be slightly different.

However, in most of the tests conducted, the friction caused by the test system itself is minimal. The results show that lower stress levels, in general, lead to higher achieved strains. On all stress levels, the NiTi wires 302 were able to achieve higher strains at the 69 MPa prestress.

FIG. 5 shows the typical strain behaviour of a NiTi wire 302 under actuation. FIG. 5 shows the mean of the actuation cycles and the standard deviation at a 95% confidence level. The width of the standard deviation is due to the diminishing strain as the material is cycled.

The strain accumulates rapidly at the beginning of the actuation but slows down when full transformation is approached. 80% of the maximum strain is achieved during the first 0.7 seconds of the 2.5 s actuation. The following 1.8 seconds (or 72%) of the actuation time only causes an additional 20% of strain. Therefore, the energy efficiency of the material can be improved by sacrificing some of the maximum strain. It has also been confirmed in multiple studies that the lifetime of SMA alloys increases if the material is only partially transformed (Lagoudas et al. 2009).

FIG. 6 shows the strain of the samples as a function of the cycle number under a stress level of 300 MPa. Increasing the nominal prestress from 30 MPa to 69 MPa increases the strain significantly. Similar behaviour was observable in all of the tested stress levels. However, it seems that increasing the prestress lowers the maximum amount of cycles before failure. More tests would be needed in order to confirm this behaviour, as no repeated test runs were performed in this study. The net force output is smaller at a higher prestress due to the fact that a greater portion of the force is required to overcome the prestress.

FIGS. 7 (a) and (b) show the effect of increasing the stress level the material has to work against while keeping the prestress constant. It seems that increasing the stress level NiTi wire 302 has to work against decreases the achieved shape memory strain. This becomes more clearly visible in FIG. 7 (b). In fact, in the tests shown in FIG. 7 (a), the 250 MPa stress gave lower strains than the test at 310 MPa. The amount of actuation cycles the material can exhibit before failure also seems to decrease with increasing stress. The test of 350 MPa at a prestress of 69 MPa differs from this trend. Further tests are needed to conclude how the increasing stress affects fatigue life.

It is evident that the maximum achievable strain diminishes quickly during the first actuation cycles. The effect is more pronounced at higher stress levels. However, between 1000 and 2000 cycles, the achievable strain stabilizes and the speed at which strain capability is lost decreases. From this point on, the material exhibits a stable, although slowly decreasing, strain until failure.

Table 1 summarizes all the results in this study. The values in Table 1 have been calculated from the points marked by symbols in FIG. 7. The first and second point on each curve represents the points used for the calculation of the shape memory strain diminishment in the beginning of the actuation cycles. Points three and four are used for the calculation of the diminishment of strain, $d\epsilon_{sme}$, in the stable region, and the last point is also the strain at failure. Again it seems that the number of cycles the material can withstand decreases as the stress level is increased.

Increasing the prestress has a similar effect. Similarly, the fast drop of strain at the beginning of the actuation cycles and its increase at higher stress levels can be seen. At all stress levels, the strain increases when going from 30 MPa to 69 MPa prestress. The rate at which strain is lost after achieving the stable strain region at 2000 cycles is negligible and the behaviour of the material remains predictable until failure.

TABLE 1

Performance data of the NiTi samples

| Stress (MPa) | Prestress (MPa) | Net stress (MPa) | Max cycles | $\epsilon_{SME}$ lost at 2000 cycles (%-p) | $\epsilon_{SME}$ at failure (%) | $d\epsilon_{SME}$ (%-p) |
|---|---|---|---|---|---|---|
| 235 | 68 | 160 | 6151 | 0.37 | 4.63 | 0.06 |
| 249 | 30 | 215 | 7701 | 0.48 | 2.83 | 0.07 |
| 305 | 27 | 276 | 7091 | 0.65 | 3.13 | 0.10 |
| 316 | 67 | 195 | 6481 | 0.74 | 3.65 | 0.11 |
| 349 | 27 | 324 | 7371 | 0.67 | 2.67 | 0.08 |
| 350 | 65 | 282 | 7601 | 0.84 | 3.14 | 0.11 |
| 379 | 67 | 310 | 4961 | 0.98 | 3.01 | 0.10 |
| 401 | 29 | 342 | 6011 | 1.04 | 2.30 | 0.10 |

Figure 8A:
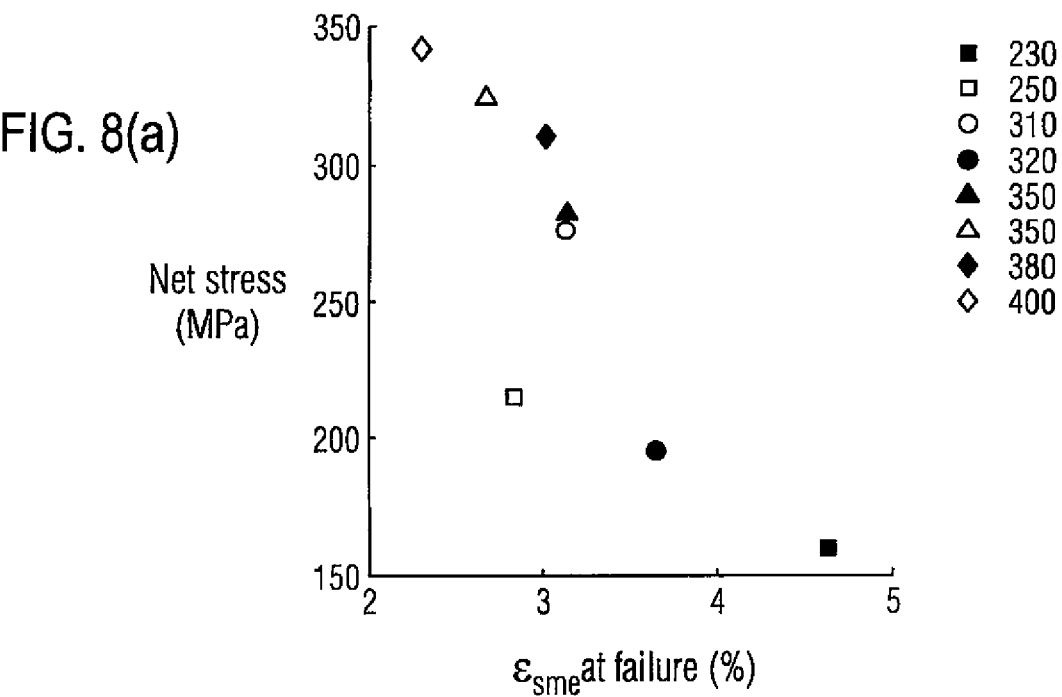

FIG. 8(a) shows the achieved strain and net stress for the different stress and prestress levels. The correlation between net output stress and strain is not straightforward. It depends greatly on the combination of stress and prestress that results in the net output. For example, an approximate net output of 320 MPa can be achieved by using two combinations from the conducted tests. When using a prestress of 27 MPa and a stress level of 349 MPa, the strain produced is 2.7%. Nearly the same output stress can be achieved with a prestress of 67 MPa and a stress level of 379 MPa, but in this case, a strain of 3% is produced.

Figure 8B:
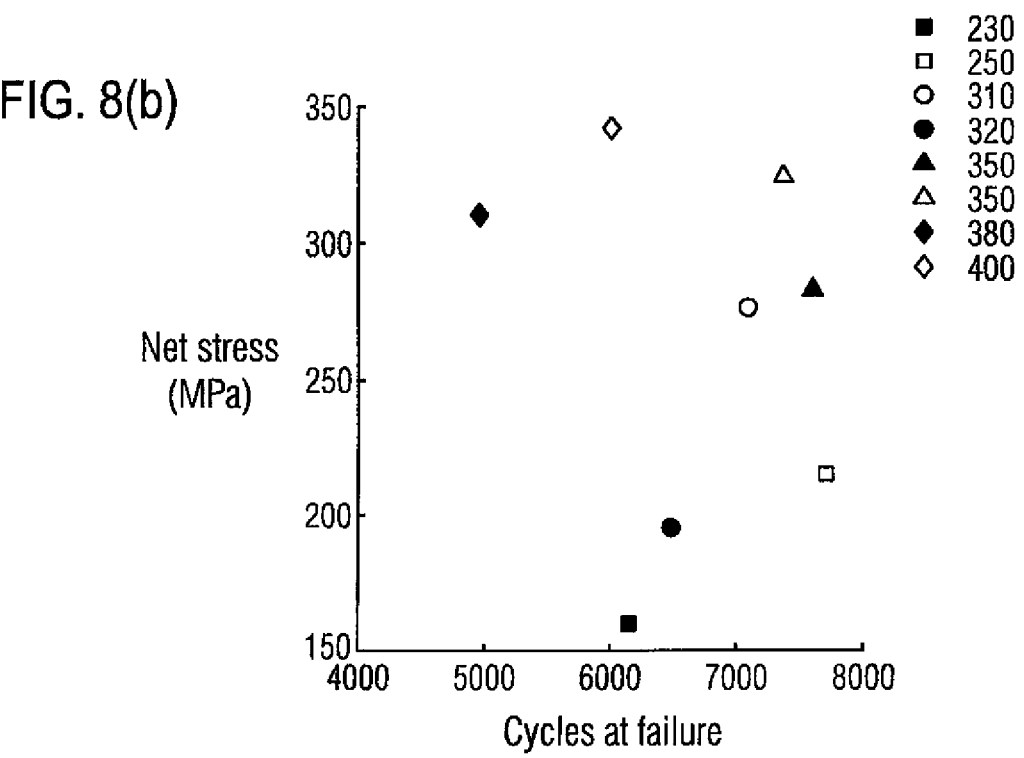

The effect the correct combination is even more pronounced when comparing the two combinations that produce a net stress output of roughly 200 MPa. The combination with the lower prestress yields a strain of under 3% while the combination with the 69 MPa prestress yields a strain of almost 4%. Then again at the 270 MPa net stress level, no significant difference can be made between the combination with lower prestress and the combination with higher prestress. On the other hand, FIG. 8(b) shows that the higher stress-prestress combinations lead to lower fatigue life.

4. Discussion

The testing system presented in this work depicts a feasible way to test the performance of NiTi wire 302 under constant load while allowing the adjustment of prestress as an independent variable. Therefore, the testing system 30 can be used to simulate the performance of the actuator concept proposed earlier under various possible configurations. Further improvements to the testing system 30 may be made to minimize the generation of friction in the load spring assembly. All samples 300 failed with a fracture at the free length of the NiTi wires 302, which indicates that the sample fixation worked as intended and no excessive stress was generated at the crimping sites.

The results obtained with the testing system 30 can be compared to published studies that evaluate the fatigue life of NiTi under constant load. Even though the alloy studied by Lagoudas et al. (2009) was NiTiCu instead of binary NiTi, the comparison can be made. Their results showed a similar evolution of the strain as the material is cycled. Especially, the sharp decline of the strain at the beginning of cycling is evident. Their results also showed that increasing the stress level leads to reduced fatigue life of the samples.

Comparing the results to those of Mammano and Dragoni (2012), who studied the functional fatigue of NiTi under various loading conditions, their constant stress cycling test does not show as sharp a drop in the beginning of the test. Their results, however, confirm that increasing the stress the NiTi element is subjected to decreases the fatigue life of the samples. At a stress level of 200 MPa, Mammano and Dragoni observed a fatigue life of 3,509-4,940 cycles, which is similar to the present results at a stress level of 400 MPa. However, in their case, the full stress of 200 MPa also acted as a prestress to the material, and in the present study the prestress was adjusted separately. This supports the hypothesis that increasing the prestress the NiTi is subjected to decreases the fatigue life.

The results of this study have several implications for realizing the actuator as discussed in more detail in the following. Applications in which the heating efficiency is important, for example in medical implant devices, the use of partial transformation is preferred. Heating the material until full transformation is achieved is inefficient because the accumulation of strain slows considerably when approaching the point of full transformation. This leads to generation of excess heat while achieving a small change in the maximum strain. As pointed out earlier, partial transformation has also been found to increase the fatigue life of the material.

The rapid decrease of strain during the beginning of actuation cycles on a new NiTi element would lead to poor predictability of actuator behaviour unless it is taken into account. When building an actuator, especially if high stress levels are employed, it is beneficial to age the elements by cycling before use. After the initial sharp drop in the achieved strain, the material behaves predictably. This is especially important in constructing an actuator according to the concept presented, as the accumulation of plastic martensitic strain would lead to a change in the prestress the NiTi is subjected to. If the accumulation of this plastic strain is sufficiently large, the actuator will seize working.

There are many combinations of prestress and stress levels that can achieve the same force output from NiTi. It is clear that the selection of the combination affects the achieved performance. From the tested prestress values of 69 MPa and 30 MPa, the 69 MPa prestress led to higher strain output at all stress levels. It is possible to reach higher strains at a certain output force level by utilizing a higher stress and prestress. However, at the same time, the maximum cycle life of the material has to be sacrificed.

Further studies may be necessary to test the performance of the NiTi at different stress and prestress values in order to find the optimal stress-prestress combinations for different applications.

5. Conclusions

We have implemented a testing system 30 that allows the testing of NiTi wire 302 under constant stress with the free adjustment of prestress as an independent variable. Then we have used testing system 30 to study the performance of NiTi wires 302 under high stress levels from 250 MPa to 400 MPa at two different prestress values of 30 MPa and 69 MPa. From the results, we conclude that 69 MPa prestress leads to higher strains at all stress levels compared to the prestress of 30 MPa. In addition, we can show that utilizing a partial transformation may increase the energy efficiency of the material if some of the maximum strain can be sacrificed. We have also found that in order to generate a predefined force output from the material, several different stress-prestress combinations can be used. The selection of the combination has profound implications on the achieved maximum strain and fatigue life. Further studies may be carried out to find the optimal combinations for different strain and fatigue life requirements.

The actuator concept presented is beneficial in many applications, where a high force output and predictable strain output are needed. The test results show that NiTi could be utilized in the manner the concept describes. However, in order to fully evaluate the concept, the actuator should be realized and tested separately. This is mainly due to the fact that the proposed concept does not allow the adjusting of the prestress during testing, unlike the testing system used in this work.

EXEMPLARY EMBODIMENTS OF OUR ACTUATORS

1) First Embodiment (FIGS. 1, 10 and 14)

Certain details of actuator 10 illustrated in section in FIG. 1 and FIG. 14 and schematically in FIG. 10 have already been discussed above. NiTi element 11 comprising a crimps 161, 162 at both of its ends is arranged to run through a preload spring 12. Crimps 161, 162 may be pressed around the NiTi element 11, or they can be integrally formed, especially by suitable processing, e.g. by turning or milling or by using a suitable chip removing process.

The preload spring 12 acts as stress-to-tension transformator 18. Preload spring 12 and NiTi element 11 are confined in housing 14 having as actuator output one or at least one movable member 13. In FIG. 1 only opening 1113 for movable member 13 is shown, the movable member 13 is in place in FIG. 14.

Instead of NiTi element 11 that is preferably of Flexinol® but that in general may be replaced by one or more converters of material that exhibits shape-memory-alloy performance, but here we discuss our actuator 10 with the help of the exemplary NiTi element 11 for the sake of clarity.

NiTi element 11 configured to cause a motion of the at least one movable member 13 in a first direction, upon NiTi element 11 undergoing thermally induced phase transition from martensite to austenite state which makes it contracted, and in a second direction that is opposite to the first direction, upon NiTi element 11 undergoing phase transition from austenite to martensite state caused by temperature change and enhanced by preload spring 12 which makes NiTi element 11 elongated.

It must be understood that housing 14 of actuator 10 acts as restrictor that has been configured to restrict the movement of NiTi element 11.

Preload spring 12 in its initial state is preloaded with a preloading force that preferably lies in the range of 250 to 450 MPa (in particular in the range between 300 and 350 MPa) during actuation and the tensile stress caused on the NiTi elements in its martensite state is in the range from 20 to 90 MPa (in particular in the range between 67 to 71 MPa), and limited by the housing 14 (more generally, any restricting arrangement could be used) in such a manner that the tension resulting from the tensile force in the NiTi element 11 is smaller than the preloading force of the preload spring 12.

2) Second Embodiment (FIGS. 9, 11, 12, 13, and 15 to 17)

FIG. 9 is a schematic drawing of actuator 110, 120 according to the second embodiment of our actuator.

FIG. 11 shows a section of a first actuator 110 according to the second embodiment and FIG. 12 a section of a second actuator 120 according to the second embodiment. FIG. 13 shows a section of a further actuator 130 and illustrates how the restrictor can be located in such a manner that it limits the movement of the spring and not the movement of the NiTi element 11.

FIGS. 15 to 17 illustrate the cycle from initial phase of the actuator 120, through movement in the first direction to the contracted phase and through movement in the second direction back to the initial phase. It should be understood that the movement cycle of actuator 110 is same to that of actuator 120.

In FIG. 11 we see that actuator 110 comprises NiTi element 11 that is confined in housing 14. It should be understood that housing 14 continues beyond the first crimp 161 but that part of the housing 14 has been omitted to improve clarity.

Actuator 110 has in the housing 14, around NiTi element 11 a pre-tensioning tube 112 that is connected to restrictor 111 that works as inhibiting unit.

Actuator 110 further comprises a movable member 13 that is configured to work as preloading compression-to-tension transformator arranged to transform the preloading force of the preload spring 12 to tensile force of the NiTi element 11. As movable member 13 we have used a bar that extends through preload spring 12.

We see in FIGS. 11 and 12 that while in the actuator 10 according to the first embodiment the preload spring 12 was configured to transform the preloading force of the preload spring 12 to tensile force of the NiTi element 11, in actuator 110, 120 the transformation is carried out by the preloading compression-to-tension transformator (movable member 13) that connects the preload spring 12 and crimp 162 of NiTi element 11.

We also see in FIGS. 11 and 12 that while in the actuator 10 according to the first embodiment the housing 14 was configured to restrict the elongation of the NiTi element 11 and in this manner to restrict the tension caused by the tensile force, in actuator 110, 120 the restriction is implemented by restrictor 111 or by restrictor 121 that is an intermediate wall.

FIG. 13 illustrates actuator 130. Now instead of using intermediate wall 1319 as restrictor, the end of housing 14 acts as restrictor 19. In other words, restrictor 19 is located in such a manner that it limits the movement of spring 12 and not the movement of the NiTi element 11.

In FIG. 15, actuator 120 is shown in its initial state. This means that preload spring 12 is also in its initial state.

FIG. 16 illustrates actuator 120 after the first phase transition of NiTi element 11, i.e. after movable member 13 has been pulled in a first direction. Between FIGS. 15 and 16 the phase transition of NiTi element 11 has occurred: NiTi element 11 has been heated, which has caused a thermally induced phase transition from martensite to austenite state which has made NiTi element 11 contracted.

NiTi element 11 has contracted by distance Δk and movable member 13 has been displaced by distance Δm. Usually, Δk=Δm but this is not necessary. If Δk≠Δm this relate from load conditions of the actuator 120 to which movable member 13 may be exposed.

In FIG. 17 actuator 120 has returned from state illustrated in FIG. 16 to its initial state. This means that the movable member 13 has been pushed in a second direction that is opposite to the first direction. NiTi element 11 has undergone phase transition from austenite to martensite state caused by temperature change and enhanced by preload spring 12 making NiTi element 11 elongated.

We see that the work done by actuator 120 through movable member 13 in the second transition (i.e. between FIGS. 16 and 17) is, under load conditions, done by movable member 13 exerting force that is at the beginning effectively the preloading force of preload spring 12 minus tension force of NiTi element 11. During the transition, the preloading force is slightly reduced (depending on Δm at each instance) and the tension force is also slightly reduced (depending on Δk at each instance).

By suitably selecting the preloading force and tension force, basically any desired force output from actuator 10, 110, 120 may be obtained.

However, we have found out that NiTi elements 11 behave individually. Also preload spring 12 material we have used seems to exhibit large variations in its elasticity and therefore we have observed the spring constant of preload springs 12 to vary strongly even between individual units of actuators 10, 110, 120 we have tried to manufacture in series.

So we have invented a method for compensating for manufacturing or material tolerances of actuators 10, 110, 120, and improved our actuators 10, 110, 120 so that the manufacturing or material tolerances are compensable in an assembled unit.

We can utilize restrictors 121, 111 to even out or to compensate for manufacturing tolerances.

The restrictor 121 as shown in actuator 120 can be assembled in housing 14 after the characteristics of preload spring 12 and/or NiTi element 11 have been measured. Easiest, the restrictor 121 is implemented by a welded dot that is welded in housing at appropriate distance to produce a suitable combination of preloading force of preload spring 12 and tensile force on NiTi element 11. If the preload stress is too small, the dot 121 is placed from a reference point towards the end of actuator 120 that increases the preload stress, and in the opposite case the dot is placed from the reference point to the opposite direction.

Assembly 110 is even more easy to manufacture. Restrictor 111 that can be implemented as inhibiting unit such as a plate is brought in place and attached to pre-tensioning tube 112. We can supply the pre-tensioning tube 112 with a thread. If the restrictor 111 is threaded, we can by rotating adjust the preload stress (and simultaneously the tensile force). The thread ensures that the restrictor 111 is held in place by a form-locking mechanism.

It may be possible to delay the exertion of pushing force by actuator 10, 110, 120 by arranging movable member 13 in such a manner that at the beginning of the second transition (i.e. situation according to FIG. 16) the movable member 13 is retracted in housing 14. During the transition, movable member 13 protrudes from housing the distance Δl. Difference Δm−Δl may be adjusted by changing the length or positioning of movable member 13 to dimensions of housing 14.

Common to actuators 10, 110, 120, 130 according to the first and the second embodiment is that NiTi element 11 has been fixed to housing 14 also from the end of housing 14 that is opposite to the side of movable member 13, or restricted in such a manner from the opposite than when the NiTi element 11 contracts, its side that is opposite to the side of movable member 13 cannot substantially move.

The purpose of the fixing or the restricting is to ensure that when NiTi element 11 contracts, the NiTi element 11 shall substantially move only from the side of movable member 13. The fixing can be carried out by welding NiTi element 11 and/or crimp 161 to housing 14, or alternatively or in addition to welding by glueing, by wedging, by compressing or by any other suitable means. Restricting, which may be in place in addition to or instead of the fixing, can be carried out with restrictor 183, for example.

In the first and second embodiments, instead of using one NiTi element 11, a bundle of NiTi elements can be used as well. Then crimps 161, 162 most preferably are arranged within connecting units 1818, 1819, the structure of which is discussed below.

3) Third Embodiment (FIG. 18)

FIG. 18 illustrates certain components of actuator 180 that comprises two individual actuators assembled next to each other in the housing. Generally, the number of individual actuators may also be larger than two.

Actuator 180 shown in FIG. 18 has been implemented by using actuators 130 previously discussed. However, with only minor modifications, actuators 130 can be replaced with any of actuators 10, 110, 120.

Actuator 180 may in particular be used as actuator of a scoliosis treatment device.

Instead of one NiTi element 11 we now preferably have a bundle 1811 of wires or rods made of or consisting shape-memory-alloy, such any number larger than one of NiTi elements. In practice, NiTi elements 11 of the above kind or other options as already discussed can be used as the elements in the bundle.

The individual elements in the bundle 1811 are electrically connected to each other in series or parallel and mechanically arranged in parallel as bundle 1811. This is exactly the same approach as chosen in the variant of the first and second embodiments discussed earlier where a bundle is used comprising a number of NiTi elements 11.

With the bundle 1811, much larger mechanical contractive forces can be exerted than with a single element alone. An "individual element" referred to here may, of course, encompass a number of NiTi wires that are in parallel both mechanically and electrically. The bundles 1811 are most preferably connected electrically in series, alternatively, they can be connected electrically in parallel.

The electrical connection between the elements in bundle 1811 is implemented by connecting units 1818, 1819 located in the respective crimp 162, 161. Restrictors 121 are configured to restrict the tensile force of the bundle 1811 by restricting the movement of the connecting unit 1818, 1819 in the work direction of the preloading spring 12. Restrictors 121 can be in pairs so that the movable member 13 can go between the individual restrictors 182. Restrictors 183 keep the bundles 1811 in place.

The individual actuators 130 in actuator 180 are electrically cross-connected to each other via cross-connect member 181 that most preferably is of biocompatible material. In this manner, the bundles 1811 can be connected electrically in series, or if desired, in parallel.

In addition, the actuator 180 comprises at least two connecting terminals 186 electrically connected to the bundle 1811 for feeding electrical energy received by at least one inductive coil in the actuator 180 to the bundle 1811. So, when the coil (not shown in FIG. 18) is energized, all elements in both bundles 1811 get warmed up and the phase transition takes place as already explained.

Preferably, restrictors 121 are implemented pair-wise in such a manner that movable member 13 is confined between restrictors 182. Cups 184, 185 are preferably implemented as one part that advantageously joins them through base part 1899.

4) Fourth Embodiment (FIGS. 19-25)

FIG. 19 illustrates actuator 190 that comprises a number of converters around an axis. Also here, the converters have been implemented by using actuators 130 previously discussed. However, with only minor modifications, actuators 130 can be replaced with any of actuators 10, 110, 120.

Actuator 190 is particularly advantageous as actuator of a bone distraction actuator i.e. as an internal osteodistraction device.

Actuator 190 may comprise any number of converters, most preferably there are between 2 and 8 such converters.

Bundles 1811 are again cross-connected in the manner explained with reference to actuator 180, except that now the connecting between the bundles of upper and lower individual actuators are electrically cross-connected by conducting plates 2013, 2014 and series connectors 2018, 2019 that most preferably is of biocompatible material.

Restrictor 111 preferably has at least one opening in the middle such that the movable member 13 can move back and forth through the opening.

Connecting cable from the inductive coil (as explained with reference to FIG. 18 already) is most preferably fed via cable recess 1992. The cable recess 1992 can be located in part 199 of the actuator 190 that is to be connected to implants' outer shell 197. The outer shell 197 is required in the current implementation because the restrictor 111 is a part of it. However, we can replace this construction with any other previously implemented manner to move restrictor.

Actuator 190 may be connected to force transmission via connection 198 to force transmission, in particular via a thread, and be connected from its other end via connection thread 1991.

FIGS. 20, 23 and 24 illustrate the bone distraction actuator 190 and FIG. 21 section A-A of it. FIG. 22 is a zoomed view C of spring stack 3 end of the distraction actuator 190. FIG. 25 illustrates sections D-D and E-E at locations illustrated in FIG. 24.

When bone distraction actuator 190 is assembled, lower NiTi holder 6 is attached to end block 5 in such a way that they are galvanically isolated from each other. End block 5 attaches to outer shell 197 that may be a tube in such a way that they form a non-separable body. One or more insulating parts 8, 9, 10 are attached to lower NiTi holder 6. The function of insulating parts 8, 9, 10 is to insulate NiTi bundles 102, 103 from NiTi holder 6. Two conducting plates 2013, 2014 are in contact with lower NiTi holder 6. The function of conducting plates 2013, 2014 is to connect NiTi bundles 100, 101 to holder 6 in such a way that electric current can flow between NiTi bundles 100, 101 and NiTi holder 6.

NiTi bundles 102, 103 are attached to coil connectors 2011, 2012 which are used to connect NiTi bundles 102, 103 to receiving coil assembly 2. Receiving coil assembly 2 comprises a coil housing 21, coil wire 23 and ferrite 22 or any other suitable material to focus the external magnetic field. However, receiving coil assembly 2 does not need to contain all these parts and only coil wire 23 is needed in the most basic case. Receiving coil assembly 2 may be replaced with a battery and a remote controllable switch, for example.

The other end of NiTi bundles 100, 101, 102, 103 is connected to upper NiTi holder 7. Between the ends of NiTi bundles 100, 101, 102, 103 are series connectors 2018, 2019 (e.g. connection plates) which form the electrical connection between the adjacent bundles. Below series connectors 2018, 2019 there are again insulations 2015, 2016 that galvanically isolate upper NiTi holder 7 from NiTi bundles 100, 101, 102, 103. Insulating part 17 is also used for this purpose.

The electrical connection is implemented as follows: Coil wire 23 connects from one end to coil connector 2011. Coil connector 2011 connects to NiTi bundle 103. NiTi bundle 103 connects to series connector 2019. Series connector 2019 connects to NiTi bundle 100. NiTi bundle 100 connects to conduction plate 2013. Conduction plate 2013 connects to lower NiTi holder 6. Lower NiTi holder 6 connects to conduction plate 2014. Conduction plate 2014 connects to NiTi bundle 101. NiTi bundle 101 connects to series connector 2018. Series connector 2018 connects to NiTi bundle 102. NiTi bundle 102 connects to coil connector 2012. Coil connector 2012 connects to the other end of the coil wire 23 and the connection path for full series connection of the NiTi bundles 100, 101, 102, 103 is complete.

Upper NiTi holder 7 is connected to a spring guide 4 through suitable means, for example thread or welding in order to achieve a rigid construction, or more preferably, a form-locking construction. The end of the spring guide 4 not connected to lower NiTi holder 7 compresses spring stack 3 against outer shell 197. Spring stack 3 may consist of disc springs or it can be a compression spring or any other construction, assembly or material that provides similar functions to a spring.

When assembling the bone distraction actuator 190, when NiTi bundles 100, 101, 102, 103 are under no tension, there exists a small gap between restrictor 111 (which preferably is implemented as middle wall of outer shell 197 especially if the outer shell 197 is implemented as a tube or tube-like structure) and upper NiTi holder 7. When NiTi bundles 100, 101, 102, 103 are tensioned by placing spring stack 3 into the bone distraction actuator 190 and tensioning the spring stack 3, NiTi bundles 100, 101, 102, 103 come under tension according to Hooke's law. The length of the gap in the non-tensioned state therefore determines the amount of stress (tension) that each NiTi bundle 100, 101, 102, 103 will be under when the bone distraction actuator 190 is assembled.

It should be noted that no matter what the load the spring stack 3 is tensioned to, NiTi bundles 100, 101, 102, 103 will only be tensioned to the amount defined by the gap. Therefore it is possible to design the bone distraction actuator 190 so that NiTi bundles 100, 101, 102, 103 are always under optimal tension (or at least close to it) prior to actuation and once they start to actuate (lower NiTi holder 7 separates from restrictor 111) it will start generating some other predetermined, preferably higher, force.

The actuation cycle of the bone distraction actuator 190 proceeds as follows: an external magnetic field induces a voltage to coil wire 23, or, alternatively, if no receiving coil assembly 2 is used, the battery is switched on.

This voltage is applied over NiTi bundles 100, 101, 102, 103 as described earlier in the electrical connection pathway. This voltage generates a current according to Ohm's law that will run through NiTi bundles 100, 101, 102, 103. The power dissipated in NiTi bundles 100, 101, 102, 103 then heats the NiTi bundles 100, 101, 102, 103 resistively. The heating causes a phase transition from the martensite phase to the austenite phase in NiTi bundles 100, 101, 102, 103. The phase transition causes NiTi bundles 100, 101, 102, 103 to contract (their length gets shorter). When this happens, NiTi bundles 100, 101, 102, 103 pull upper NiTi holder 7 towards lower NiTi holder 6 and upper holder 7 separates from restrictor 111. This will in turn pull spring guide 4 towards lower NiTi holder 6. This will cause spring stack 3 to compress (its length gets shorter) because the gap between outer shell 197 and spring guide 4 shortens.

Now, when the external magnetic field is switched off (or, alternatively, the battery is switched off) there is no current flowing in NiTi bundles 100, 101, 102, 103. This allows NiTi bundles 100, 101, 102, 103 to cool down and transform from the austenite phase back to the martensite phase, assisted by spring stack 3. At the same time spring guide 4 moves back to its original position and spring stack 3 compression returns to the original level. At the same time the bone distraction actuator 190 provides an output force if measured from the left-hand end of spring guide 4 in FIG. 20 i.e. at connection 198 to force transmission. Spring guide 4 can be connected from connection 198 to force transmission to suitable power transmission methods in order to generate movement from the repeating contraction pulses of the power transfer mechanism. In particular, this may be any such power transfer mechanisms disclosed in 2009/115645 A1 and WO 2011/148047 A1. Especially we here mean the mechanisms described in any of the referred documents for converting a reciprocal movement to extending movement in one direction.

The many features and advantages of the present invention are apparent from the written description. Further, since numerous modifications and changes will be readily apparent to those skilled in the art, the invention should not be limited to the exact construction and operation as illustrated and described. Hence, all suitable modifications and equivalents may be resorted to as falling within the scope of the invention.

5) An Alternative Construction of the Actuator (FIG. 26-28)

FIGS. 26 and 27 show an alternative construction of the actuator. The actuator contains four bundles of NiTi wires (3001) that are electrically connected in series with a receiving power transfer cable (3017), that may be a receiving coil via cable. The electrical circuit of the actuator is completed with several elements, that are described below.

The inductive power transfer cable (3017) connects to the inductive power transfer coil (not shown).

The other end of the cable (3017) connects to the NiTi element (3111). The contact may be done by crimping. The contact may also be done by soldering. Further, the contact may be done by welding. The NiTi element (3111) is resting on a lifting plate (3015) whose function is to make the NiTi elements (3111-3114) sit on equal heights such that they distribute the load on the small crimp on the underlying insulation more evenly.

The NiTi element (3111) connects to the NiTi element (3112) through the series connection plate (3014).

The NiTi element (3112) further connects to the NiTi element (3113) through the series connection plate (3016).

The NiTi element (3113) further connects the NiTi element (3114) through the series connection plate (3141).

The NiTi element (3114) further connects to the other pole of the inductive power transfer coil through identical wires to the ones of the power transfer cable (3017).

The parts (3010), (3011), (3012) and (3013) act as insulations that insulate the metallic parts of the power source from the electrical circuit. They are also for preventing the short circuits. The insulation may be made of any electrically insulating material. The insulation may ge e.g. of polymer or ceramic material. The insulation (3013) further acts as a heat barrier that slows the transmission of heat from inside the power source to the power source housing tube (3004).

The NiTi elements (3111-3114) are placed between the movable member (3002) and a fixed support structure (3003). The fixation of the support structure (3003) is achieved through the actuators housing tube (3004), spring support plate (3005) and actuator support tube (3006). The free end (left side in FIG. 26) of the support tube (3006) is fixed in place. A spring compression rod (3007) which may also be in more general called as a rod connects to the movable member (3002). These can also be manufactured as a single part. A compression spring stack (3009) is placed around the spring compression rod (3007) so that they are resting against the spring support plate (3005). The spring compression rod (3007) is pulled to the optimal prestress for the NiTi elements and a fixation part (3008) is added. The added fixation part (3008) then preferably holds the optimal prestress. This can be fastened by any means, e.g. by thread or welding etc.

Alternatively, instead of fixing the support tube (3006) on its place, the support tube 3006 can be excluded. In that case, the actuator should be fixed with the support structure (3003), housing tube (3004) or spring support plate (3005).

As the compression spring stack (3009)tries to elongate and is blocked by the fixation part (3008), the force is transferred through the spring compression rod (3007) to the movable member (3002). The movable member (3002) further tries to move to the left in FIG. 26 causing the force to be transferred to the NiTi elements (3111-3114). The other end of the NiTi elements (3111-3114) rests on the support structure (3003) which takes the load and transfers it through the tubes (3004, 3006) and the spring support plate (3005) to the fixation point at the left end of the part (3006) in FIG. 26.

Alternatively, instead of a compression spring stack (3009) a normal compression spring can be used. Alternatively instead of a compression spring stack (3009) or compression spring a tension spring can be used. When using a tension spring the tension spring is connected to the end of the rod (3007). When pulling the tension spring from the other end, the spring causes the rod (3009) to move and to exert stress on the NiTi elements (3111-3114). When the tension spring is pulled to optimal prestress it can be fixed to the part (3006) using any kind of fixation means.

The operation cycle of the actuator is explained by FIG. 28. In resting state the measure $L_1$ may be e.g. 19.70-19.90 cm, preferably 19.80 cm, measure $L_2$ may be e.g. 19.90-20.10 cm, preferably 20.00 cm and the measure $L_3$ may be e.g. 22.90-23.10 cm, preferably 23.00 cm.

When the external magnetic field is activated, a voltage is induced in the inductive power transfer coil. The power transfer coil further leads to a current going through the inductive power transfer cables (3017) and the series electrical circuit of the actuator containing NiTi elements (3111-3114). The NiTi elements are further heated through resistive heating. This causes the NiTi elements to go through a phase change from martensite to austenite phase. This causes the NiTi elements to contract. The contraction moves the movable member (3002) to the right by the amount of the contraction. The contraction may be subtracted by any elastic deformations in the structures. The contraction also causes the spring compression rod (3007) to move to the right by the same amount. This in turn causes the compression spring stack (9) to compress further.

Now the actuator has fulfilled its actuation step. Now, the measure $L_1$ may be e.g. 18.70-18.90 cm, preferably 18.80 cm, measure $L_2$ may be e.g. 18.90-19.10 cm, preferably 19.00 cm and the measure $L_3$ may be e.g. 23.90-24.10 cm, preferably 24.00 cm.

As the left side of the support tube (3006) is fixed, the actuator is able to produce a displacement and force output through the right end of the movable member (3002). Subsequently, the magnetic field is turned off and the NiTi elements (3111-3114) cool down. As a consequence, the compression spring stack (3009) pulls the NiTi elements to the original position. Also the movable member (3002) moves back to the original position. The actuator is ready for a new actuation cycle.

By connecting the actuator to a one way movement permitting element a distraction osteogenesis device extendable with aid of the magnetic fields can be realized.

LIST OF REFERENCE NUMERALS USED 2 receiving coil assembly
3 spring stack
4 spring guide (acts as movable member 13)
5 end block
6 NiTi holder
7 NiTi holder 8, 9, 10 insulating part
10 actuator
11 NiTi element
12 preload spring
13 movable member
14 housing
16 empty volume
17 insulating part
18 preloading force-tension transformer
19 restrictor (end wall)
21 coil housing
22 ferrite
23 coil wire
30 testing system
31 compression rod
32 connection to load cell
33 electrical connection
34 spring locking clamp
35 connection to hydraulic actuator
37 extensometer for strain measurement
100, 101, 102, 103 NiTi bundles
110 actuator
111 restrictor (inhibiting unit)
112 pre-tensioning tube
120 actuator
121 restrictor (intermediate wall)
130 actuator
161 crimp
162 crimp
180 scoliosis treatment actuator
181 cross-connect member
183 restrictor
184, 185 cup in which crimp is set during assembly
186 connecting terminal
190 bone distraction actuator
195 connector
197 implant's outer shell, optional part of the actuator 190
198 connection to force transmission
199 part of the actuator to be connected to implant's outer shell
300 test sample
301 crimp
302 NiTi wire
1113 opening for movable member
1811 bundle
1818 connecting unit
1819 connecting unit
1840 mechanical connection piece
1899 base part
1991 connection thread
1992 cable recess
2011, 2012 coil connectors
2013, 2014 conducting plate
2015, 2016 insulation
2018 series connectors
2019 series connectors
3000 actuator
3001 NiTi wire
3002 movable member
3003 support structure
3004 housing tube
3005 spring support plate
3006 actuator support tube
3007 rod
3008 fixation part
3009 compression spring stack
3010, 3011, 3012, 3013 insulating parts
3014, 3016 series connection plates
3015 lifting plate
3017 power transfer cable
3111, 3112, 3113, 3114 NiTi elements
3141 series connection plate
$L_1$ length of the spring stack
$L_2$ dislocation parameter of the compression rod
$L_3$ dislocation parameter of the movable member

CITED LITERATURE

Aalsma A M M, Hekman E E G, Stapert, J W J L, Grootenboer H J 1997 The Design of A TiNi actuator in an intramedullary leg lengthening device J. PHYS. IV FRANCE 7 C5 627-631

Aalsma A M M, Hekman E E G, Staper J, Grootenboer H 1998 A completely intramedullary leg lengthening device Proc. of the 20th Ann. Int. Conf. of the IEEE Engineering in Medicine and Biology Society 20-5 2710-2713

Belson A 2013, patent publication U.S. Pat. No. 8,361,090 B2, Apparatus and method for endoscopic colectomy Bertacchini O W, Lagouds D C, Patoor E 2009 Thermomechanical transformation fatigue of TiNiCu SMA actuators under a corrosive environment—Part Experimental results Int J Fatigue 1571-1578

Chau E T F, Friend C M, Allen D M, Hora J, Webster J R 2006 A technical and economic appraisal of shape memory alloys for aerospace applications Mater. Sci. Eng., A 438-440 589-592

Dynalloy Inc. 2012 Technical charactreristics of Flexinol® actuator wires manufacturers datasheet, retrieved online 2012-10-12 from http://www.dynalloy.com/pdfs/TCF1140.pdf Dahlgren J M 2009, patent application publication US 2009076597 A1, System for mechanical adjustment of medical implants Elwaleed A K, Mohamed N A, Nor M J, Mustafa M M 2007 A new concept of a linear smart actuator Sens. Actuators, A 135 244-249

Fumagalli L, Butera F, Coda A 2009 SmartFlex NiTi wires for shape memory actuators J. Mater. Eng. Perform. 18 691-695

Helsinki University of Technology 2009, patent application publication WO 2009115645 A1, Internal osteodistraction device Horst M, Hayoz D, Borghi E, Tozzi P 2013, patent application publication US 20130096586 A1, Medical device comprising an artificial contractile structure Kheirikhah M M, Rabiee S, Edalata M E 2011 A Review of shape memory alloy actuators in robotics Lecture Notes in Computer Science 6556 206-217

Kim E, Yoo Y, Lee J 2008 Development of a NiTi actuator using a two-way shape memory effect induced by compressive loading cycles Sens. Actuators, A 148 437-442

Lagoudas D C, Miller D A, Rong L, Kumar P K 2009 Thermomechanical fatigue of shape memory alloys Smart Mater. Struct. 18

Mammano G S, Dragoni E 2012 Functional fatigue of Ni—Ti shape memory wires under various loading conditions Int J Fatigue http://dx.doi.org/10.1016/j.ijfatigue.2012.03.004

Mertmann M, Vergani G 2008 Design and application of shape memory actuators Eur. Phys. J. Special Topics 158 221-230

Olympus Corp. 2012, patent application publication EP 2133566 A2, Shape memory alloy actuator Takahashi M 2009 patent application publication US 2009013684 A1, Shape memory alloy actuator Ryhanen J 1999 Biocompatibility evaluation of nickel-titanium shape memory alloy Dissertation for University of Oulu ISBN 951-42-5221-7

Soubeiran A A 2003, patent application publication US 2003032958 A1, Device for relative displacement of two bodies Stolz-Irion R 2009, patent application publication DE 102007036359 A1, Implantatvorrichtung zur Gewebe- und/oder Knochendistraction sowie Verfahren zum Betreiben einer solchen

The invention claimed is:

1. Actuator comprising at least one shape-memory-alloy based converter in a housing and at least one preload spring and
   configured to cause a motion of at least one movable member in a first direction, upon the at least one converter undergoing thermally induced phase transition which makes it contracted, and
      in a second direction that is opposite to the first direction, upon the at least one converter undergoing phase transition caused by temperature change and enhanced by the preload spring which makes the converter elongated;
characterized by
a rod connecting to the said movable member and to a spring, wherein the spring is one of a compression spring stack placed around the rod or a tension spring connecting to the end of the rod;
and wherein the rod is pullable to the optimal prestress by one of elongating the compression spring stack or pulling the tension spring, for the converter such that a fixation part is addable for one of blocking the compression spring stack or fixing the tension spring to a part.

2. Actuator according to claim 1, wherein the at least one converter comprises at least one bundle of individual wires or rods made of shape-memory-alloy in such manner that in the bundle the individual wires are electrically connected to each other in parallel and mechanically arranged in parallel.

3. Actuator according to claim 2, further comprising at least two connectors electrically connected to each said bundle for feeding electrical energy received from a power source to the bundle.

4. Actuator according to claim 3 wherein said power source includes a wireless switchable battery.

5. Actuator according to claim 3 wherein the electrical energy is received through at least one inductive coil.

6. Actuator according to claim 2, wherein the electrical and mechanical connection between the individual wires of the bundle is implemented within at least one connecting unit.

7. Actuator according to claim 2 wherein if there is more than one bundle, the bundles are connected to each other electrically in series or in parallel.

8. Actuator according to claim 7 wherein the bundles are connected to each other mechanically in parallel.

9. Actuator according to claim 1 wherein the motion of at least one movable member is achieved with aid of a fixed support structure, a housing tube, and a spring support plate.

10. Actuator according to claim 9 wherein the motion of at least one movable member is additionally achieved with a support tube.

11. Actuator according to claim 1 wherein the converters are based on NiTi elements connected through the series connection plates.

12. Method for improving the actuator of claim 1, characterized by pulling a rod connecting to the said movable member and to a spring to the optimal prestress by one of elongating the compression spring stack or pulling the tension spring, for the converter and adding a fixation part for one of blocking the compression spring stack or fixing the tension spring to a part.

* * * * *